US011628310B2

(12) United States Patent
Marsteller

(10) Patent No.: US 11,628,310 B2
(45) Date of Patent: Apr. 18, 2023

(54) METHODS, SYSTEMS, AND COMPOSITIONS FOR MAINTAINING FUNCTIONING DRAINAGE BLEBS ASSOCIATED WITH FOREIGN BODIES

(71) Applicant: RADIANCE THERAPEUTICS, INC., Tucson, AZ (US)

(72) Inventor: Laurence J. Marsteller, Tucson, AZ (US)

(73) Assignee: RADIANCE THERAPEUTICS, INC., Tucson, AZ (US)

( * ) Notice: Subject to any disclaimer, the term of this patent is extended or adjusted under 35 U.S.C. 154(b) by 616 days.

(21) Appl. No.: 16/810,204

(22) Filed: Mar. 5, 2020

(65) Prior Publication Data
US 2020/0197725 A1 Jun. 25, 2020

Related U.S. Application Data

(63) Continuation-in-part of application No. PCT/US2018/049400, filed on Sep. 4, 2018.

(30) Foreign Application Priority Data

Sep. 7, 2017 (GB) .................................. 1714392.6

(51) Int. Cl.
*A61N 5/10* (2006.01)
*A61F 9/007* (2006.01)
*A61F 9/00* (2006.01)

(52) U.S. Cl.
CPC .......... *A61N 5/1017* (2013.01); *A61F 9/0017* (2013.01); *A61F 9/00709* (2013.01); *A61F 9/00781* (2013.01); *A61N 5/103* (2013.01)

(58) Field of Classification Search
CPC ... A61N 5/1017; A61N 5/103; A61F 9/00709; A61F 9/0017; A61F 9/00781
See application file for complete search history.

(56) References Cited

U.S. PATENT DOCUMENTS 1,525,158 A 2/1925 Viol
1,733,159 A 10/1929 Leach
(Continued)

FOREIGN PATENT DOCUMENTS

CA 643082 A 6/1962
DE 1149134 B 5/1963
(Continued)

OTHER PUBLICATIONS

JF Kirwan, PH Constable, IE Murdoch, and PT Khaw. "Beta Irradiation: new used for an old treatment: a review". Eye (2003) 17, 207-215. (Year: 2003).*
(Continued)

*Primary Examiner* — Christine H Matthews
*Assistant Examiner* — Joshua Daryl D Lannu
(74) *Attorney, Agent, or Firm* — Nguyen Tarbet LLC

(57) ABSTRACT

Methods, systems, and compositions for maintaining functioning drainage blebs to reduce intraocular pressure (IOP) of an eye being treated for glaucoma. The methods, systems, and compositions feature the combination of a minimally invasive glaucoma surgery (MIGS) implant or procedure and the application of beta radiation to the bleb. The beta radiation can function to inhibit or reduce the inflammation and/or fibrogenesis that typically occurs after insertion of a MIGS implant and leads to bleb failure. By reducing inflammation and/or fibrogenesis, the MIGS implant and the blebs can remain functioning appropriately.

12 Claims, 9 Drawing Sheets

(56) References Cited

U.S. PATENT DOCUMENTS

| | | | |
|---|---|---|---|
| 2,559,793 | A | 1/1949 | Pregel |
| 2,517,568 | A | 8/1950 | Hissong |
| 3,602,959 | A | 9/1971 | Perez et al. |
| 5,637,073 | A | 6/1997 | Freire |
| D387,162 | S | 12/1997 | Zeimer |
| 6,050,970 | A | 4/2000 | Baerveldt |
| D441,447 | S | 5/2001 | Hjertman et al. |
| 6,274,614 | B1 | 8/2001 | Richter et al. |
| 6,443,881 | B1 | 9/2002 | Finger |
| 6,875,165 | B2 | 4/2005 | Dejuan, Jr. et al. |
| 7,070,554 | B2 | 7/2006 | White et al. |
| D621,508 | S | 8/2010 | Bindra |
| D642,266 | S | 6/2011 | Marsteller et al. |
| 8,430,804 | B2 | 4/2013 | Brigatti et al. |
| D691,270 | S | 10/2013 | Marsteller et al. |
| D702,346 | S | 4/2014 | Ben Nun |
| D731,058 | S | 6/2015 | Dietrich |
| D731,060 | S | 6/2015 | Little, III |
| D747,806 | S | 1/2016 | Wargner et al. |
| D752,749 | S | 3/2016 | Van Dalen et al. |
| D755,970 | S | 5/2016 | Bergmanson |
| D756,515 | S | 5/2016 | Chin et al. |
| D795,427 | S | 8/2017 | Korenfeld et al. |
| 10,022,558 | B1 | 7/2018 | Marsteller et al. |
| D933,225 | S | 10/2021 | Marsteller et al. |
| D933,226 | S | 10/2021 | Marsteller et al. |
| 2002/0115902 | A1 | 8/2002 | Dejuan, Jr. et al. |
| 2004/0138515 | A1 | 7/2004 | White |
| 2005/0277802 | A1 | 12/2005 | Larsen et al. |
| 2006/0111605 | A1 | 5/2006 | Larsen et al. |
| 2007/0265485 | A1 | 11/2007 | DeJuan et al. |
| 2008/0300444 | A1 | 12/2008 | Ye et al. |
| 2009/0124955 | A1* | 5/2009 | Ayyala ............... A61F 9/0017 604/521 |
| 2009/0216062 | A1 | 8/2009 | Axelrod et al. |
| 2010/0000449 | A1 | 1/2010 | Brigatti et al. |
| 2010/0004581 | A1 | 1/2010 | Brigatti et al. |
| 2011/0004045 | A1 | 1/2011 | Larsen et al. |
| 2013/0006033 | A1 | 1/2013 | Cipriani et al. |
| 2013/0211178 | A1 | 8/2013 | Brigatti et al. |
| 2015/0105605 | A1 | 4/2015 | Finger et al. |
| 2015/0265850 | A1 | 9/2015 | Finger et al. |
| 2016/0151643 | A1 | 6/2016 | Roder |
| 2017/0112520 | A1 | 4/2017 | Lavi et al. |
| 2017/0216499 | A1 | 8/2017 | Kaplan |
| 2017/0258988 | A1 | 9/2017 | Meyer et al. |
| 2018/0229055 | A1 | 8/2018 | Marsteller |
| 2018/0296855 | A1 | 10/2018 | Lohrenz et al. |
| 2019/0240504 | A1 | 8/2019 | Brachman et al. |
| 2019/0290643 | A1 | 9/2019 | Ni et al. |
| 2020/0101318 | A1 | 4/2020 | Marsteller |
| 2020/0171323 | A1 | 6/2020 | Marsteller et al. |
| 2020/0197725 | A1 | 6/2020 | Marsteller |

FOREIGN PATENT DOCUMENTS

| | | |
|---|---|---|
| EP | 1529554 B1 | 2/2006 |
| EP | 1997532 A1 | 12/2008 |
| EP | 3031494 B1 | 8/2018 |
| FR | 4398 E | 7/1905 |
| GB | 2551706 A | 1/2018 |
| JP | S63138962 A | 6/1988 |
| JP | 2001507969 A | 6/2001 |
| JP | 2011508654 A | 3/2011 |
| JP | 2016512101 A | 4/2016 |
| RU | 134056 U1 | 11/2013 |
| WO | WO9850092 | 11/1998 |
| WO | WO200158346 A1 | 8/2001 |
| WO | 2004098523 A2 | 11/2004 |
| WO | 2005079915 A1 | 9/2005 |
| WO | 2009075714 A1 | 6/2009 |
| WO | 2009149175 A1 | 12/2009 |
| WO | 2010022153 A1 | 2/2010 |
| WO | WO2013186779 A2 | 12/2013 |
| WO | WO2015057531 A2 | 4/2015 |
| WO | WO2015105539 A3 | 7/2015 |
| WO | WO2016178746 A1 | 11/2016 |
| WO | WO2017112891 A1 | 6/2017 |
| WO | WO2018060983 A1 | 4/2018 |
| WO | WO2019050863 A1 | 3/2019 |
| WO | WO2019164940 A1 | 8/2019 |

OTHER PUBLICATIONS

W Assmann, M Schubert, A Held, A Pichler, A Chill, S Kiermaier, K Schlosser, H Busch, K Schenk, D Streufert, I Lanzi. "Biodegradable radioactive implants for glaucoma filtering surgery produced by ion implantation". Nuclear Instruments and Methods in Physics Research B 257 (20007) 108-113 (Year: 2007).*

JF Kirwan, S Cousens, L Venter, C Cook, AStulting, P Roux, I Murdoch. "Effect of B radiation on success of glaucoma drainage surgery in South Africa: randomised controlled trial". BMJ (published Oct. 5, 2006). doi:10.1136/bmj.38971.395301.7c downloaded from http://www.bmj.com on Oct. 2018 (Year: 2006).*

Schultz et al. "Growth factors and ocular wound healing." Eye 8.2 (1994): 184-187.

Kirwan et al. "Beta irradiation: new uses for an old treatment: a review." Eye 17.2 (2003): 207-215.

Khaw et al. "Modulation of wound healing after glaucoma surgery." Current opinion in ophthalmology 12.2 (2001): 143-148.

Sanoculis LTD, MIMS Procedure, http://www.sanoculis.com/category/mims-procedure (2014) 2 pages.

Kumar et al. Minimally invasive micro sclerostomy may be alternative to trabeculectomy. Ocular Surgery News U.S. Edition, May 10, 2016, 4 pages.

Cook et al. "Randomised clinical trial of trabeculectomy with mitomycin-C versus trabeculectomy with beta radiation." South African Ophthalmology Journal 13.4 (2018): 11-14.

Egbert, "Glaucoma in West Africa: a neglected problem." British journal of ophthalmology 86.2 (2002): 131-132.

Khaw et al. "Effect of beta radiation on proliferating human Tenon's capsule fibroblasts." British journal of ophthalmology 75.10 (1991): 580-583.

Wilder, el. al. "Pterygium treated with excision and postoperative beta irradiation." International Journal of Radiation Oncology* Biology* Physics 23.3 (1992): 533-537.

Kirwan et al. "Beta radiation in glaucoma surgery (Review)" Cochrane Database of Systematic Reviews (2012).

G Hay-Smith et al. "Beta radiation: an effective and potentially cheap aid to preventing sight loss from glaucoma, 2010." Conference proceedings. 3 pages.

Lai et al. "Trabeculectomy with β radiation: Long-term follow-up." Ophthalmology 110.9 (2003): 1822-1826.

Quigley et al. "The number of people with glaucoma worldwide in 2010 and 2020." British journal of ophthalmology 90.3 (2006): 262-267.

Mpyet et al. "Site of trabeculectomy and control of intraocular pressure: a preliminary report." Nigerian Journal of Surgical Research 4.3 (2002): 94-97.

Kirwan et al. "Effect of β radiation on success of glaucoma drainage surgery in South Africa: randomised controlled trial." Bmj 333.7575 (2006): 942.

George et al. "Glaucoma in India: estimated burden of disease." Journal of glaucoma 19.6 (2010): 391-397.

Venkatesh et al. "Glaucoma care in India." Glaucoma Today (2013): 37-39.

Dhalla et al. "Is beta radiation better than 5 flurouracil as an adjunct for trabeculectomy surgery when combined with cataract surgery? A randomised controlled trial." PloS one 11.9 (2016): e0161674.

George et al. "Prevalence of glaucoma in India: a review." J Curr Glaucoma Pract 1.2 (2007): 7-11.

Technical Information and Instruction Manual for users of Beta Therapy Source Model 67-S50, Nuclear Associates, Carle Place, NY. Copyright 1979, 14 pages.

(56) References Cited

OTHER PUBLICATIONS

Soares "Comparison of NIST and manufacturer calibrations of 90Sr+ 90Y ophthalmic applicators." Medical Physics 22.9 (1995): 1487-1493.

Bahrassa et al. "Postoperative beta radiation treatment of pterygium." International Journal of Radiation Oncology* Biology* Physics 9.5 (1983): 679-684.

Castroviejo. "New masks to limit the active surface of radiation in beta ray applicators." Transactions-American Academy of Ophthalmology and Otolaryngology. American Academy of Ophthalmology and Otolaryngology 60.3 (1956): 486.

Zhang et al., "In vivo cross-sectional observation and thickness measurement of bulbar conjunctiva using optical coherence tomography" Investigative ophthalmology & visual science 52.10 (2011): 7787-7791.

Wells et al. "Comparison of two clinical bleb grading systems." Ophthalmology 113.1 (2006): 77-83.

Dhingra et al. "The moorfields safer surgery system." Middle East African journal of ophthalmology 16.3 (2009): 112.

Constable et al. "The effects of single doses of 3 radiation on the wound healing behaviour of human Tenon's capsule fibroblasts." British journal of ophthalmology 88.2 (2004): 169-173.

Assmann et al. "Biodegradable radioactive implants for glaucoma filtering surgery produced by ion implantation." Nuclear Instruments and Methods in Physics Research Section B: Beam Interactions with Materials and Atoms 257.1-2 (2007): 108-113.

Ayyala et al., Early Follow-Up after Xen Implantation Needed. Ocular Surgery News U.S. Edition, Mar. 5, 2018, 1 page.

Ayyala et al., Xen Gel Stent Early Results: Safety and Efficacy in the Short Term. AGS 2018 Annual Meeting. Mar 4, 2 pages.

Howlet et al., "Bulbar conjunctival and Tenon's layer thickness measurement using optical coherence tomography." Journal of current glaucoma practice 8.2 (2014): 63.

NRC "Information Notice 96-66: Recent Misadminitrations Caused by Incorrect Calibrations of Strontium-90 Eye Applicators", United States Nuclear Regulatory Commission, Office of Nuclear Material Safety and Safeguards, Washington D.C. 20555, Dec. 13, 1996, 4 pages.

Nilsen, PhD, Department of Physics and Scientific Computing Group University of Oslo, N-0316 Oslo, Norway in Spring 2008, 14 pages.

Kirwan et al. "Beta radiation in glaucoma surgery" 2012, 2 pages.

J.E. Gentle, Monte Carlo Methods in Statistics, International Encyclopedia of Education (Third Edition) 2010.

Kirwan et al. "Beta irradiation: new uses for an old treatment: a review" Eye, 2003; 17:207-215 (doi: 10.1038/sj.eye.6700306) p. 207, col. 2, para 2; p. 208, col. para 2; col. 2, para 1, 3; p. 211, col. 2, para 1-2; p. 1-2; p. 212, col. 1, para 1; p. 213, col. 1, para 1; Fig 2.

Kirwan et al. "Effect of β radiation on success of glaucoma drainage surgery in South Africa: randomized controlled trial" BMJ 2006; 333-942 (doi: 10.1136/bmj.38971.395301) whole document.

Constable et al. "The effects of single doses of 0 radiation on the wound healing behaviour of human Tenon's capsule fibroblasts" Br J Ophthalmol. 2004; 88:169-173 (doi: 10.1136/njo.2003.0203388) whole document.

Assmann et al. "Biodegradable radioactive implants for glaucoma filtering surgery produced by ion implantation" Nucl Instrum Meth B. 2007; 257(1-2):108-113 (doi: 10.1016/j.nimb2006.12.155) whole document.

Khaw et al., "Modulation of wound healing after glaucoma surgery" Current Opinion in Opthalmolgy, 2001; 12:143-148 Lippincott Williams & Wilkins, Inc.

Schuliz et al., "Growth Factors and Ocular Wound Healing" Eye, 1994, 8, 184-187, Royal College of Ophtalmologists.

Erickson et al. "The American College of Radiology and the American Brachytherapy Society practice parameter for the performance of radionuclide-based high-dose-rate brachytherapy." Brachytherapy 16.1 (2017): 75-84.

Cordeiro, M. F., L. Chang, and P. T. Khaw. "The healing of ocular tissues: The basis of successful treatment of ocular disease." (2000): 101-110.

Schuliz et al. Growth Factors and Ocular Wound Healing. Eye (1994) 8, 184-187.

Kirwan et al. Beta irradiation: new uses for an old treatment: a review. Eye(2003) 17, 207-215.

Khaw et al. Modulation of wound healing after glaucoma surgery. Curr Opin Ophthalmol. Apr. 2001;12(2):143-8.

Kumar et al. Minimally invasive micro sclerostomy may be alternative to trabeculectomy. Ocular Surgery News U.S. Edition, May 10, 2016 . https://www.healio.com/ophthalmology/glaucoma/news/print/ocular-surgery-news/%7Be1be2619-cca2-40cb-8ff4-28062463f4ee%7D/minimally-invasive-micro-sclerostomy-may-be-alternative-to-trabeculectomy.

Cook et al. Randomised clinical trial of trabeculectomy with mitomycin-C versus trabeculectomy with beta radiation. SA Ophthalmology Journal, Spring 2018 • vol. 13 | No. 4. pp 11-14.

Peter Egbert, Glaucoma in west Africa: a neglected problem, Br J Ophthalmol 2002, 86, pp. 131-132.

P T Khaw, S Ward, I Grievson, N S C Rice, Effect of Beta radiation on proliferation human Tenon's capsule fibroblasts, Br J Ophthalmology, 1991, 75, 580-583.

R Wilder, et al. Pterygium treated with excision and postoperative beta irradiation, Int. J. Radiation Oncology Viol. Phys., 1992, vol. 23, pp. 533-537.

James F Kirwan, Christina Rennie, Jennifer R Evans, Beta radiation for glaucoma surgery (Review), Cochrane Database of Systematic reviews 2012, Issue 6. Art. No. CD003433, published Jun. 13, 2012. http://www.cochrane.org/CD003433/EYES_beta-radiation-in-glaucoma-surgery.

G Hay-Smith, J Kiran, C Usher, I E Murdoch, Beta radiation: an effective and potentially cheap aid to preventing sight loss from glaucoma, 2010 . Conference proceedings. https://www.semanticscholar.org/paper/Beta-radiation%3A-an-effective-and-potentially-cheap-Hay-Smith-Kirwan/7da123cef3f6203697a584af35561ae3d00306a1 https://pdfs.semanticscholar.org/7da1/23cef3f6203697a584af35561ae3d00306a1.pdf.

Jimmy S. Lai, Agnes S. Poon, Clement C. Tham, Dennis S. Lam, Ophthalmology, Sep. 2003, vol. 110, Issue 9, pp. 1822-1826. https://www.ncbi.nlm.nih.gov/pubmed/13129883.

H A Quigley, AT Broman, The number of people with glaucoma worldwide in 2010 and 2020, Br J Ophthalmol 2006 (90) 262-267.

C D Mpyet, S K Alli, N E Zaure, Site of trabeculectomy and control of intraocular pressure: a preliminary report, The Nigerian Joural of Surgical research vol. 4, No. 3-5, Jul.-Dec. 2002, pp. 94-97.

J F Kirwan, S Cousins, L Venter, C Cook, A Stunting, P Roux, I Murdoch, BMJ, Effect of beta radiation an success of glaucoma drainage surgery in South Africa: randomized controlled trial, doi:10.1136/bmj.38971.395301.7C (published Oct. 5, 2006).

R J Venkatesh, K Palanisway, Glaucoma care in India, Glaucoma Today, Jan./Feb. 2013, pp. 37-39.

Kazoo Dhalla, Simon Cousens, Richard Bowman, Mark Wood, Ian Murdoch, PLOS One, Sep. 8, 2016. http://journals.plos.org/plosone/article?id=10.1371/journal.pone.0161674.

Technical Information and Instruction Manual for users of Beta Therapy Source Model 67-850, Nuclear Associates, Carle Place, N.Y. Copyright 1979.

Soares CG. Comparison of NIST and manufacturer calibrations of 90Sr+90Y ophthalmic applicators. Med Phys 1995, 22(9): 1487-1493.

Bahrassa and Datta. Postoperative beta radiation treatment of pterygium. Int J Radiat Oncol Biol Phys 1983, 9(5):679-84.

Castroviejo. Trans Am Acad Ophthalmol Otolaryngol. 1956, 60(3):486.

Zhang et al., In Vivo Cross-Sectional Observation and Thickness Measurement of Bulbar Conjunctiva Using Optical Coherence Tomography Investigative Ophthalmology & Visual Science 2011, 52(10):7787-7791.

Wells AP, Ashraff NN, Hall RC, et al. Comparison of two clinical bleb grading systems. Ophthalmology 2006; 113:77-83. Abstract.

Dhingra S, Khaw PT. The Moorfields Safer Surgery System. Middle East African Journal of Ophthalmology. 2009;16(3):112-115.

(56) References Cited

OTHER PUBLICATIONS

Invitation to Pay Additional Fees issued for PCT Application No. PCT/US18/49400 dated Nov. 1, 2018.
UKIPO Examination Opinion and Search Report issued for GB Application No. GB1714392.6 dated Feb. 16, 2018.
Constable et al. "The effects of single doses of beta radiation on the wound healing behaviour of human Tenon's capsule fibroblasts" Br J OphthalmoL 2004; 88:169-173 (doi:1 0.1136lbjo.2003.020388).
Assmann et al. "Biodegradable radioactive implants for glaucoma filtering surgery produced by ion implantation" Nucl Instrum Meth B. 2007; 257(1-2):108-113 (doi:10.1016/j.nimb.2006.12.155).
International Search Report issued for PCT Application No. PCT/US18/49400 dated Jan. 2, 2019.
Ayyala et al. Early Follow-Up After Xen Implantation Needed. Ocular Surgery News U.S. Edition, Mar. 5, 2018. https://www.healio.com/ophthalmology/glaucoma/news/online/%7B4f090e9a-4661-42a7-a8b7-4fa0cd690316%7D/early-follow-up-after-xen-implantation-needed.
Ayyala et al. Xen Gel Stent Early Results: Safety and Efficacy in the Short Term. AGS 2018 Annual Meeting. Mar. 1-4. https://ags.planion.com/Web.User/AbstractDet?ACCOUNT=AGS&CONF=AM18&ABSID=11997.
Howlet J et al., Journal of Current Glaucoma Practice 2014, 8(2):63-66.
NRC Information Notice 96-66: United States Nuclear Regulatory Commission, Office of Nuclear Material Safety and Safeguards, Washington D.C. 20555, Dec. 13, 1996.
K. Nilsen, PhD, Department of Physics and Scientific Computing Group University of Oslo, N-0316 Oslo, Norway in Spring 2008.

\* cited by examiner

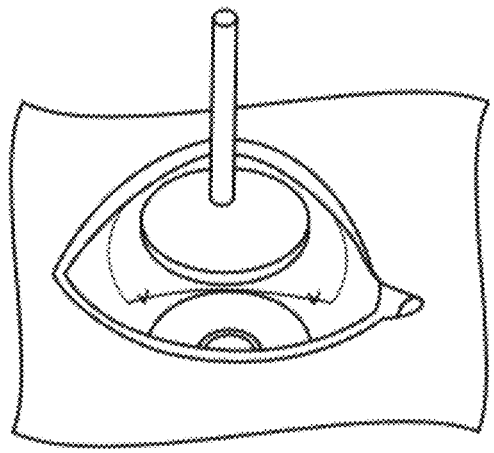
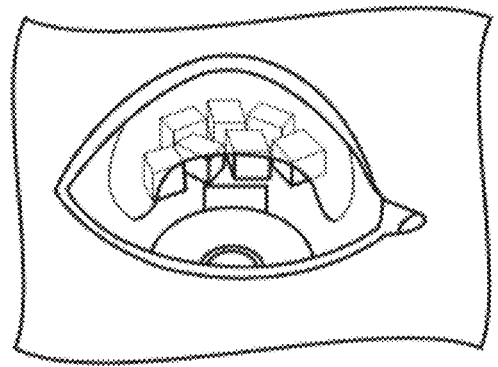
FIG. 5A  FIG. 5B
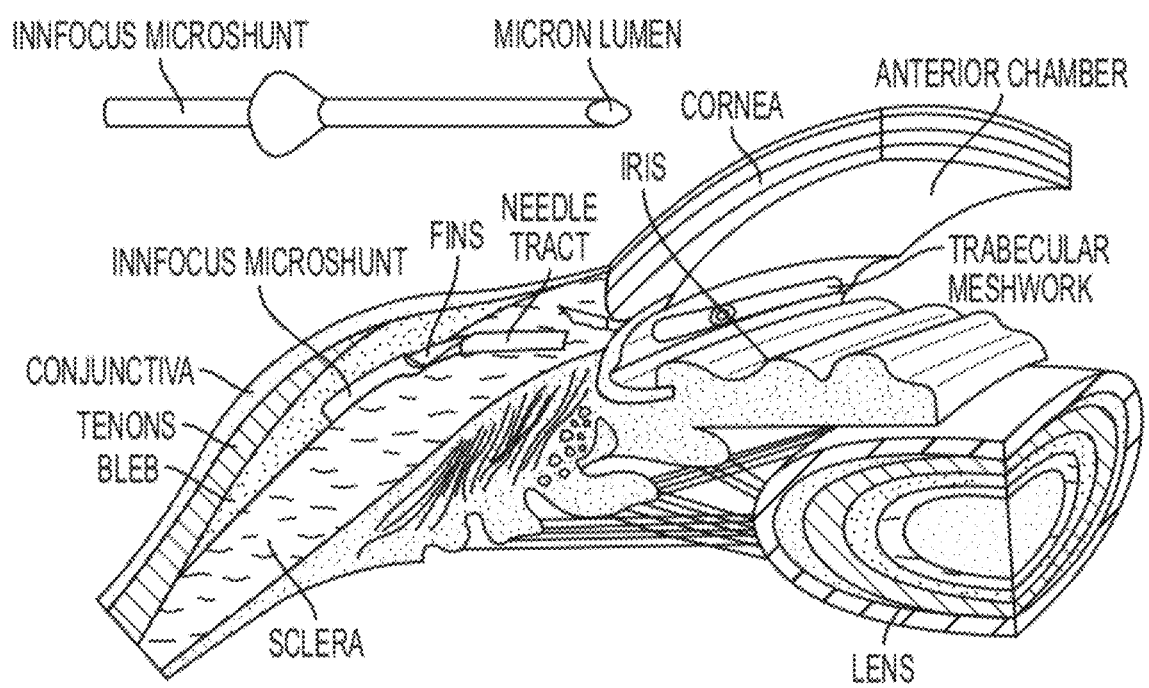
FIG. 6

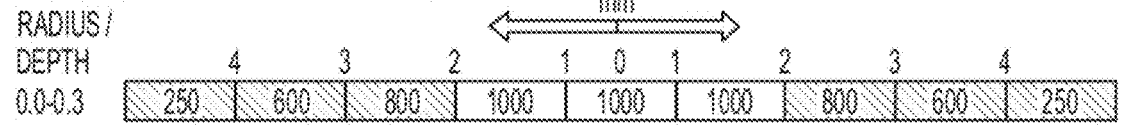
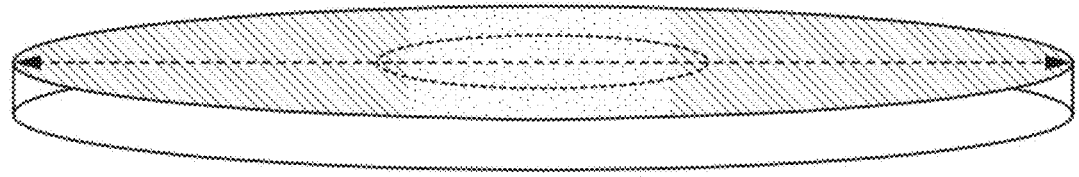
FIG. 12
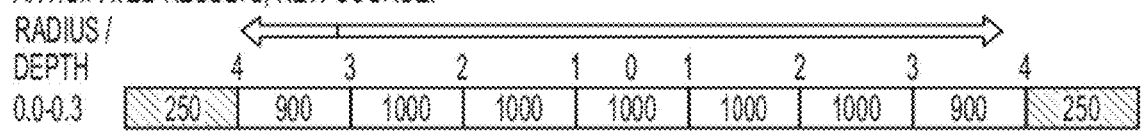
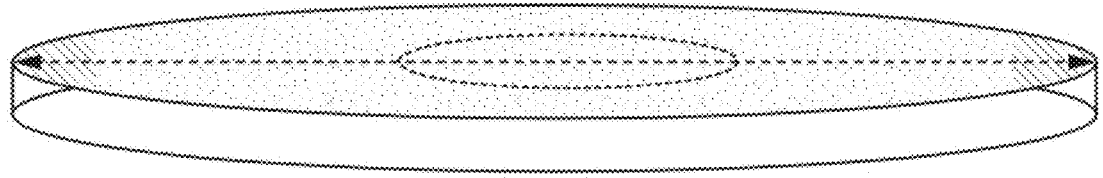
FIG. 13

RADIOLYSIS OF INTRACELLULAR WATER ($H_2O$)

METHODS, SYSTEMS, AND COMPOSITIONS FOR MAINTAINING FUNCTIONING DRAINAGE BLEBS ASSOCIATED WITH FOREIGN BODIES

CROSS REFERENCE

This application is a continuation-in-part and claims benefit of PCT Application No. PCT/US18/49400 filed Sep. 4, 2018, which claims benefit of UK Patent Application No. 1714392.6 filed Sep. 7, 2017, the specifications of which are incorporated herein in their entirety by reference.

FIELD OF THE INVENTION

The present invention relates to methods, systems, and compositions for treating glaucoma treatment-associated drainage blebs, such as those associated with foreign bodies, with beta radiation to maintain functioning blebs. The present invention also relates to the use of a Minimally Invasive Glaucoma Surgery (MIGS) implant for treating glaucoma.

BACKGROUND OF THE INVENTION

Glaucoma

Glaucoma is the leading cause of irreversible blindness and represents a family of diseases with a characteristic optic neuropathy (see FIG. 1). Therapy for this group of diseases is principally focused at reducing the intraocular pressure (IOP) of the fluid inside the eye (aqueous humor), thus averting ongoing damage to the optic nerve. Two thirds of cases are classified as Primary Open Angle Glaucoma (POAG). POAG develops slowly and usually without any symptoms. Initially, glaucoma affects peripheral or side vision, but it can advance to central vision loss. If left untreated, glaucoma leads to significant irreversible vision loss in both eyes, and blindness.

Glaucoma is managed by attempting to lower the intraocular pressure (IOP). In the USA, Europe, and some other industrialized countries, the first line therapy is typically medication delivered by eye drops. Such medications include beta-blockers, prostaglandins, alpha-adrenergic agonists, and carbonic anhydrase inhibitors. For patients who fail medication and in other parts of the world where there are economic and distribution barriers to the practicality of daily medication and frequent follow up, the treatment regime is primarily surgical interventions.

The most common surgical procedure for the treatment of glaucoma is called a trabeculectomy (see FIG. 2). This allows drainage of the aqueous humor from within the eye via a guarded trapdoor to a small reservoir or channel (termed the "bleb") above the sclera and under or in the conjunctiva, where it is absorbed.

A recent development in the practice of glaucoma treatment is the use of Minimally Invasive Glaucoma Surgery (MIGS) implants. Most MIGS implants are ab interno devices, that is, devices which are implanted from the inside of the eye. The majority of these devices channel the aqueous humor to either the Schlemm's canal or to the supraciliary space. A subset of MIGS devices is the class of conjunctiva-involving MIGS shunts that pierce through the sclera to a drainage bleb. These implants replace the time consuming and skill-requiring creation of a trabeculectomy by the use of flow-controlled devices, which may be more easily placed to connect the anterior chamber to a bleb in the sub-conjunctival space. These MIGS implants have the potential to replace trabeculectomy as the leading surgical treatment for glaucoma. Selective laser trabeculoplasty may be used alone or to augment various therapies, as can ab-interno microshunts to Schlemm's canal or the supraciliary space.

Despite compelling therapeutic advantages over nonsurgical treatments, drainage surgery and devices are clinically limited by postoperative scarring. For example, one of the primary complications of MIGS implants is the failure of blebs by scar formation or wound reversion, which leads to poor drainage and thus a reduction in the therapeutic effect of the MIGS implant. Attempts to address this include the application of antimetabolites such as mitomycin C (MMC) and 5-fluorouracil (5FU) (see FIG. 5B). These antimetabolites are used in liquid form and are delivered either by injection or by placing microsurgical sponges soaked in the drug directly onto the operative site underneath the conjunctiva.

One of the problems associated with antimetabolites (e.g., MMC and 5FU) is that they do not preserve MIGS-associated blebs well. By some reports, the failure rate by three or five years approaches 50%. The present invention provides the unique technical feature of the use of beta radiation instead of antimetabolites in combination with MIGS. Beta radiation surprisingly preserves blebs better than antimetabolites and is not obvious for the reasons stated herein.

Radiation Physics

A radioactive isotope, known as a radionuclide or radioisotope, is an element that has an unstable nucleus and emits radiation during its decay to a stable form. There may be several steps in the decay from a radioactive to a stable nucleus. There are four types of radioactive decay: alpha, beta negative, beta positive, and electron capture. Gamma rays can be emitted by the daughter nucleus in a de-excitation following the decay process. These emissions are considered ionizing radiation because they are powerful enough to liberate an electron from another atom.

Therapeutic radionuclides can occur naturally or can be artificially produced, for example by nuclear reactors or particle accelerators. Radionuclide generators are used to separate daughter isotopes from parent isotopes following natural decay.

Non-limiting examples of radioactive isotopes following one of the four decay processes are given herein: (1) Alpha decay: radium 226, americium 241; (2) Beta minus: iridium 192, cesium 137, phosphorus 32 (P-32), strontium 90 (Sr-90), yttrium 90 (Y-90), ruthenium 106, rhodium-106; (3) Beta positive: fluorine 18; (4) Electron capture: iodine 125, palladium 106. Examples of gamma emission include iridium 192 and cesium 137.

Half-life is defined as the time it takes for one-half of the atoms of a radioactive material to disintegrate. Half-lives for various radioisotopes can range from a few microseconds to billions of years.

The term activity in the radioactive-decay processes refers to the number of disintegrations per second. The units of measure for activity in a given source are the curie (Ci) and becquerel (Bq). One (1) Becquerel (Bq) is one disintegration per second. An older unit is the Curie (Ci), wherein one (1) Ci is $3.7 \times 10^{10}$ Bq.

Brachytherapy

According to the American Association of Physicists in Medicine (AAPM), brachytherapy is "the clinical use of small encapsulated radioactive sources at a short distance from the target volume for irradiation of malignant tumors or nonmalignant lesions." According to the US Federal Code of Regulations, a Radionuclide Brachytherapy Source (RBS) is "a device that consists of a radionuclide what may be enclosed in a sealed container made of gold, titanium, stainless steel, or platinum and intended for medical purposes to be placed onto a body surface or into a body cavity or tissue as a source of nuclear radiation for therapy." Other forms of brachytherapy sources are also used in practice. For example, a commercially available conformal source is a flexible, thin film made of a polymer chemically bound to phosphorus-32 (P-32). Also available is a radiotherapy treatment for hepatocellular carcinoma (HCC) that consists of millions of microscopic, radioactive glass microspheres (20-30 micrometers in diameter) containing Yttrium-90. Other forms of brachytherapy employ x-ray generators as sources instead of radioisotopes.

Generally, in medical practice, brachytherapy can be categorized as topical or plaque brachytherapy, intracavitary, and interstitial.

Some implementations of brachytherapy employ permanently implanted RBSs. For example, in Low Dose Rate (LDR) brachytherapy for prostate cancer, a standard of care treatment, radioactive Iodine-125 RBSs are placed directly into the prostate where they remain indefinitely.

In another implementation, High Dose Rate (HDR) brachytherapy TheraSpheres are infused into the arteries that feed liver tumors. These microspheres then embolize, lodging themselves in the liver's capillaries and bathing the malignancy in high levels of yttrium-90 radiation. In both these implementations, the total dose is given by consuming the entire radioisotope.

Some other implementations of brachytherapy employ a transient placement of the RBS. For example, in after-loaded High Dose Rate (HDR) brachytherapy, very tiny plastic catheters are placed into the prostate gland, and a series of radiation treatments is given through these catheters. A computer-controlled machine pushes a single highly radioactive iridium-192 RBS into the catheters one by one for a specified dwell time at locations throughout the volume being irradiated. The catheters are then easily pulled out, and no radioactive material is left at the prostate gland.

Another example of transient placement of an RBS includes prophylactic therapy for restenosis of coronary arteries after stent implantation. This is a non-malignant condition that has been successfully treated by placing a catheter into the coronary artery, then inserting a HDR radioactive source into the catheter and holding it there for a predetermined time in order to deliver a sufficient dose to the vessel wall.

The present invention provides methods of treatment that feature the application of beta radiation in combination with Minimally Invasive Glaucoma Surgery (MIGS) implants (or the like) to effectively maintain functioning drainage blebs, e.g., blebs associated with foreign bodies, to help avoid scar formation or wound reversion, to inhibit or reduce the fibrogenesis and/or inflammation in the blebs, etc. As discussed in detail below, while the use of beta radiation in trabeculectomy-type glaucoma treatment has long been discouraged by experts in the field, it has been found to be surprisingly effective at preventing bleb failure when combined with use of MIGS implants.

SUMMARY OF THE INVENTION

It has been surprisingly discovered that specific methods of treatment and systems that combine Minimally Invasive Glaucoma Surgery (MIGS) implants or the like and the application of beta radiation are effective for maintaining functioning drainage blebs, e.g., by reducing or inhibiting foreign body induced scar formation or wound revision, by inhibiting or reducing fibrogenesis and/or inflammation in the bleb, etc. Unlike trabeculectomy (which is an implant-free surgical technique), MIGS procedures implant a foreign body into the eye, thus, one cannot expect that the effects of beta radiation on the scarring response will be the same in MIGS implantation and trabeculectomy surgeries. Additionally, the use of beta radiation in trabeculectomy-type glaucoma treatment has long been discouraged by experts in the field. However, beta radiation has been found to be surprisingly effective at preventing bleb failure when combined with use of MIGS implants.

Unpredictability of the Effects of Beta Radiation on MIGS Implant Foreign Body Induced Scarring Response There has been no evidence to prove that the scarring responses caused by trabeculectomy surgery and MIGS implantation are the same. In fact, there is a strong suggestion that the responses could be significantly different. Therefore, a person having ordinary skill in the art would not be able to predict how beta radiation would affect the scarring responses caused by a MIGS implant.

Because a MIGS implant is a foreign body implanted within the eye, there is a question of how the biocompatibility of the implant affects the scarring response. As stated in a study comparing different biomaterials for glaucoma drainage devices, "The inflammatory response following the implantation of different biomaterials in the subconjunctival space may vary and could contribute to the success or failure of the operation," (Ayyala et. al., Arch Ophthalmol. 1999; 117:233-236). A biocompatibility study on the InnFocus MicroShunt® implant (InnFocus, Inc., Santen Pharmaceutical Co.), an example of a flow-controlled stent, noted: "It is believed that the fibrotic and inflammatory reactions induced by biomaterials are a major determinant of success. Other factors such as shape, flexibility, modulus, and texture could also be associated with erosion, extrusion, inflammation, and scarring," (Acosta et. al., Arch Opthalmol. 2006; 124; 1742-1749).

An additional example of the well-documented issue of the foreign body reaction states, "[Glaucoma filtration surgery] often fails because of scarring. Various conjunctival implants have been developed to minimize the scarring but may cause a foreign body reaction and capsule formation resulting in reduced efficacy and sub-optimal pharmacokinetics," (Khaw et. al., 2015, ARVO Poster Abstract). Because of the industry expectation that the scarring responses to trabeculectomy surgery (wherein a foreign body is not implanted) and MIGS (wherein a foreign body is implanted) would not be the same, it is impossible to predict how beta radiation would affect scarring from MIGS device implantation.

Teaching Away from the Use of Beta Radiation for Glaucoma Treatment

1. Industry Expectation that Mitomycin C (MMC) is More Effective than Beta Radiation:

It would be surprising to one of ordinary skill in the art that beta radiation would be chosen over liquid antimetabolites because the prior art teaches that beta radiation is a less effective anti-metabolite than mitomycin C (MMC) and is merely similar in effectiveness to 5-fluorouracil (5FU). In brief, beta radiation has been reported to be roughly equivalent to 5FU as an anti-metabolite for glaucoma drainage surgery, and MMC has been reported to be superior to 5FU for the same use. Therefore, MMC is taught to be more effective than beta radiation as an anti-metabolite for glaucoma drainage surgery. More specifically, a 2016 study involving a trabeculectomy-type of glaucoma surgery (Dhalla et al., 2016, PLoS ONE 11(9): e0161674) concluded that: "Firstly, there is no evidence of a difference between the use of 5FU and beta radiation as an anti-metabolite in phacotrabeculectomy surgery." Additionally, a 2015 Cochrane review by Cabourne et al. (Cabourne et al., 2015, Cochrane Database of Systematic Reviews Issue 11. Art. No.: CD006259) that compared MMC and 5FU for wound healing in trabeculectomy-type glaucoma surgery concluded: "Our review showed that the risk of failure of trabeculectomy at one year after surgery was lower in those participants treated with MMC compared to those treated with 5-FU." Thus, since the effectiveness of beta radiation with trabeculectomy procedures is shown to be similar to that of 5FU and 5FU is shown to have inferior effectiveness compared to MMC, the literature teaches that MMC is a more effective anti-metabolite than beta radiation.

Furthermore, a direct comparative study of intraoperative mitomycin C (MMC) and beta radiation use in pterygium surgery indicated that, "intraoperative mitomycin C is more effective than β irradiation as an adjunctive treatment for pterygium surgery using a sliding conjunctival flap," (Amano et al., 2000, British Journal of Ophthalmology 84:618-621). Thus, the prior art teaches away from use of beta radiation and instead teaches that MMC is a more effective anti-metabolite.

2. Industry Expectation that Mitomycin C (MMC) Provides More Comprehensive Penetration than Beta Radiation:

Secondly, it is surprising to use beta radiation instead of liquid antimetabolites because the prior art teaches that liquid antimetabolites are better suited for dispersion across a wide treatment area. The importance of this wide treatment area is highlighted in the Moorfields Safe Surgery System, which was developed by Sir. Peng Khaw (Khaw et al., 2005, Glaucoma Today, March/April, 22-29). The publication that introduced the System notes that previous focal treatment with MMC led to "a thin, cystic bleb." One of the key components of the improved System is to treat "as large of an area as possible" with MMC. Critically, the publication notes: "Enlarging the surface area of treatment [with MMC] results in a more diffuse, non-cystic area, clinically. It also prevents the development of the ring of steel, which would otherwise restrict aqueous humor flow and promote the development of a raised, cystic, avascular bleb."

In stark contrast to the freely flowing and widely dispersed liquid antimetabolites, the use of beta radiation for ophthalmic applications has traditionally been extremely focused. Because reproducible dosage requires that the applicator be held in place for a specified period of time, the treatment area is set by the size of the applicator head. The typical diameter of an ophthalmic applicator head is only in the order of 10-14 mm and only a fraction of the head comprises the active diameter (reported to range from 4.3 to 8.9 mm) (Soares, 1995, Med. Phys. 22 (9), September, 1487-93). Even within the active diameter, the intensity of the dose falls off quickly with increasing distance from the center of the dose.

Additionally, beta radiation is unable to effectively penetrate tissue and is restricted to treatment of superficial areas close to the center of the applicator. This is because the intensity of the dose falls off very quickly with increased distance from the applicator. For example: "[Beta radiation] is applied during the operation using a radioactive applicator which emits beta rays which have only a very local penetration to a depth of less than one millimeter," (Kirwan et al, 2012, Cochrane Database of Systematic Reviews Art. No.: CD003433).

Testing of ophthalmic applicators in Soares et al. showed irregular dosage patterns and large variation between even the same model applicator. Many of the applicators did not even have the active portion aligned with the center of the applicator. Further, safety concerns led to the narrowing of the therapeutic area in ophthalmic applicators used for pterygium treatment by attaching a Castroviejo field-shaping masks. The effect of these masks is to provide a narrowed focal application like the one taught away from by the Moorfields Safe Surgery System. The Moorfields Safe Surgery System is considered to be a standard of care.

Thus, while antimetabolites such as MMC are freely flowing liquid solutions that can disperse across a wide area, treatment by beta radiation has been much more focally limited. The current teaching is that wide dispersion may be important for formation of a healthy diffuse bleb. Beta radiation does not have the ability to fluidly disperse across the tissue in the same manner as MMC. This limitation would prevent one having ordinary skill in the art from envisaging beta radiation as being able to effectively treat the wide area currently treated by permeation with liquid antimetabolites. Thus, the prior art teaches away from use of beta radiation and instead teaches that liquid anti-metabolites provide a more pervasive and desirable treatment. It is surprising to use a therapeutic approach that has long been associated with focal application, instead of an easily dispersed liquid.

3. Industry Fear that Beta Radiation is Associated with Cataracts:

Thirdly, it is surprising to use beta radiation instead of liquid antimetabolites because of a long history of reported correlation between beta radiation and cataracts. Beta radiation has been avoided in glaucoma treatment because of the widely held belief by leading ophthalmologists that beta radiation would cause cataracts. For example, a 2012 Cochrane review (Kirwan et al, 2012, Cochrane Database of Systematic Reviews Art. No.: CD003433) on four trials that randomized 551 people, entitled *Beta Radiation for Glaucoma Surgery*, concluded that "people who had beta irradiation had an increased risk of cataract after surgery." As an additional example: Merriam et al concluded that the minimum cataractogenic dose for a single treatment was 200 cGy to the lens epithelium, with the probability of cataract approaching unity for a dose of 750 cGy (see Merriam G R, 1965, Trans Am Ophthalmol Soc. 54: 611-653, summarized by Kirwan et al, Eye (2003) 17, 207-215. doi:10.1038/sj.eye.6700306). The literature has made clear that the medical community teaches to avoid treatment of glaucoma with beta radiation.

In the same 2003 review on beta radiation, Kirwan also described some of the negative study reports regarding use of beta radiation in ophthalmology. The review emphasized that: "Adverse effects with beta radiation for pterygium have been widely reported. Earlier reports concentrated on lens opacity, conjunctival telangiectasia, and other side effects of doses much higher than those used clinically after pterygium surgery," and that "Use of beta radiation for pterygium has diminished, with conjunctival autografting and topical mitomycin C now being widely used." Furthermore, in addition to the adverse effects noted by others, Kirwan also later reported adverse effects in his own study on the use of beta radiation for the treatment of trabeculectomy patients.

The powered, controlled and randomized study on the effect of beta radiation on success of trabeculectomy-type glaucoma surgery was published by Kirwan in 2006. Notably, the study demonstrated that, "an increased risk for cataract surgery (a known complication of trabeculectomy) in the beta radiation arm during the two years after surgery." At two years after the study the risk of developing a cataract requiring extraction was 16.7% in the radiation group and only 3.2% in the placebo group. Kirwan noted, "If beta radiation increases the need for further surgery the advantages of single therapy with trabeculectomy are much diminished."

The previously acknowledged risk and subsequent observed incidence of cataracts following the application of beta radiation was a strong discouragement against the use of beta radiation in glaucoma treatment. The randomized controlled clinical trial results revealed a notable increased incidence of cataracts associated with beta therapy; and the Kirwan authors called for an "urgent study . . . of combined surgery (trabeculectomy with beta radiation plus cataract extraction)."

Ethically-engaged research requires a commitment to universal ethical norms, such as those expressed in the Declaration of Helsinki and the Belmont Report. The World Health Organization (Research ethics committees: basic concepts for capacity-building. World Health Organization 2009) notes that, research ethics committees review proposed studies with human participants to ensure that they conform to internationally and locally accepted ethical guidelines. Review by a research ethics committee is required by international ethical standards governing research involving human participants, as well as by local law in many jurisdictions. In the light of their role in identifying and evaluating the risks and benefits of research, research ethics committees must include individuals with scientific and medical expertise. In studies involving medical interventions, research ethics committees must determine that adequate care and treatment will be provided for participants.

"Research funded by the United States of America (USA) government, regardless of the setting where the research takes place, must conform to the 'Common Rule' (45 CFR 46) that defines and regulates the scope and review of federally-funded human subjects research," (https://www.ncbi.nlm.nih.gov/pmc/articles/PMC3491753/0). "The International Council on Harmonisation (ICH) defines an institutional review board (IRB) as a group formally designated to protect the rights, safety and well-being of humans involved in a clinical trial by reviewing all aspects of the trial and approving its startup. IRBs can also be called independent ethics committees (IECs). An IRB/IEC reviews the appropriateness of the clinical trial protocol as well as the risks and benefits to study participants. RB/IEC members should be collectively qualified to review the scientific, medical and ethical aspects of the trial. An IRB/IEC should have . . . at least five members . . . . Competent members who are able to review and evaluate the science, medical aspect and ethics of the proposed trial," (http://www.ppdi.com/Participate-In-Clinical-Trials/Become-an-Investigator/Institutional-Review-Board). The US 21 CFR Part 56 (22)(c) declares that "Institutional Review Board (IRB) means any board, committee, or other group formally designated by an institution to review, to approve the initiation of, and to conduct periodic review of, biomedical research involving human subjects. The primary purpose of such review is to assure the protection of the rights and welfare of the human subjects." Both international norms, and in the US, US 21 CFR Part 56 Sec. 56.107 mandate that "Each IRB shall have at least five members . . . possessing the professional competence necessary to review the specific research activities, the IRB shall be able to ascertain the acceptability of proposed research in terms of institutional commitments and regulations, applicable law, and standards of professional conduct and practice." "In Grimes v. Kennedy Krieger Institute, Inc., a Maryland state court, although it has been criticized for doing so, honored the Nuremberg Code as "the most complete and authoritative statement of the law of informed consent to human experimentation," (emphasis added). The court then goes on to cite several authors to support what appears to be its general premise, that the Nuremberg Code should be incorporated into American common law jurisprudence to establish a clear set of duties as to the protection offered the subjects of human experimentation," (https://www.ncbi.nlm.nih.gov/pmc/articles/PMC1069025).

Following the findings of the Kirwan study of increased cataract in the beta therapy patient group, Dhalla studied the concomitant treatment regimen of beta therapy with phacoemulsification. The Dhalla human clinical study surgically removed the patients' natural lenses at the time of beta administration. The study authors argue that this protocol is ethical even in those patients in which "if the [pre-existing] cataract does not cause significant disability it would not normally warrant surgical intervention." In other words, under normal conditions these patients would not be offered cataract surgery because the local standard of care would not warrant surgical intervention. The Dhalla beta therapy protocol included the additional surgical intervention of removing the patients' natural lens because the Kirwan study findings of increased incidence of cataract with the use of beta radiation alone.

In approving the Dhalla experimental study as ethical, the human study independent ethics committee decision provides direct authoritative teaching away from the use of beta therapy as a stand-alone adjunct to glaucoma filtration surgery.

Note that the outcome results of the Dhalla experimental human study were negative. "[The] study sample size calculation was based on detecting superiority of beta-radiation over 5FU [5 fluorouracil] which was the standard treatment . . . . We detected no major difference between 5 fluorouracil and beta radiation." The disappointing study outcomes of the Dhalla study informed the medical community that beta was not superior to the antimetabolite 5FU.

The industry expectation that antimetabolites such as 5FU and MMC are more effective than beta radiation, combined with the expectation that 5FU and MMC provide more comprehensive penetration than beta radiation and the fear that beta radiation is associated with cataracts, strongly teaches away from the use of beta radiation. Thus, it would be surprising to one having ordinary skill in the art to use beta radiation with MIGS implants to maintain functioning drainage blebs for the treatment of glaucoma.

Summary of Particular Embodiments

As used herein, the term "beta radiation source" or "source of beta radiation" can refer to the term "radioisotope." In any of the methods or compositions here, the radioisotope or source of beta radiation may comprise Strontium-90 (Sr-90), Phosphorus-32 (P-32), Ruthenium 106 (Ru-106), Yttrium 90 (Y-90), or a combination thereof.

The present invention features a radioisotope that emits beta radiation, a pharmaceutical composition comprising a source of beta radiation, a radioactive composition comprising a source of beta radiation, a radioactive composition that emits beta radiation, and a radioactive source that emits beta radiation, which may be for use in a method of treating glaucoma. The present invention features a radioisotope that emits beta radiation, a pharmaceutical composition comprising a source of beta radiation, a radioactive composition comprising a source of beta radiation, a radioactive composition that emits beta radiation, and a radioactive source that emits beta radiation, which may be for use in a method of reducing or preventing scar formation in a draining bleb in a human eye being treated for glaucoma with a Minimally Invasive Glaucoma Surgery (MIGS) implant.

The present invention also features a radioisotope that emits beta radiation, a pharmaceutical composition comprising a source of beta radiation, a radioactive composition comprising a source of beta radiation, a radioactive composition that emits beta radiation, and a radioactive source that emits beta radiation, which may be for use in a method of reducing or preventing scar formation in a draining bleb associated with a foreign body in a human eye.

In some embodiments, the method comprises implanting a Minimally Invasive Glaucoma Surgery (MIGS) implant within the eye of a patient being treated for glaucoma. The implant is implanted trans-sclerally to form a bleb in the subconjunctival space or between the conjunctiva and Tenon's capsule. The method further comprises applying the beta radiation from the radioisotope or source of beta radiation (or radioactive composition, pharmaceutical composition, etc.) to a target area of the eye, wherein the target area is at least a portion of the bleb. The methods herein may be effective to maintain a functioning drainage bleb.

The present invention also features a radioisotope that emits beta radiation for use in preventing or reducing scar formation in a draining bleb in a human eye being treated or having been treated for glaucoma with a minimally invasive glaucoma surgery (MIGS) implant. The radioisotope is characterized in that the radioisotope is administered to the eye such that beta radiation from the radioisotope is applied to a target area of the eye, wherein the target area is at least a portion of the bleb. The present invention also features a radioisotope that emits beta radiation for use for use in preventing or reducing scar formation in a draining bleb associated with a foreign body, wherein the radioisotope is characterized in that the radioisotope is administered to the eye such that beta radiation from the radioisotope is applied to a target area of the eye, wherein the target area is at least a portion of the bleb.

The present invention also features a composition comprising a source of beta radiation for use in a method of preventing or reducing scar formation in a draining bleb in a human eye being treated or having been treated for glaucoma with a minimally invasive glaucoma surgery (MIGS) implant. The composition is characterized in that the composition is administered to the eye such that beta radiation from the source of beta radiation is applied to a target area of the eye, wherein the target area is at least a portion of the bleb.

The present invention also features a composition comprising a source beta radiation for use in a method of treating glaucoma in an eye wherein a Minimally Invasive Glaucoma Surgery (MIGS) implant is implanted trans-sclerally to form a bleb in the subconjunctival space or between the conjunctiva and Tenon's capsule. The composition is characterized in that the composition is applied to the eye such that beta radiation from the source of beta radiation is applied to a target area of the eye, wherein the target area is at least a portion of the bleb.

The present invention also features a radioactive composition comprising a source of beta radiation for use in a method of treating glaucoma. In some embodiments, method comprises implanting a Minimally Invasive Glaucoma Surgery (MIGS) implant within the eye of a patient being treated for glaucoma, wherein the implant is implanted trans-sclerally to form a bleb in the subconjunctival space or between the conjunctiva and Tenon's capsule; and applying the beta radiation from the source of beta radiation to a target area of the eye, wherein the target area is at least a portion of the bleb. The methods herein may be effective to maintain a functioning drainage bleb. The radioactive composition (e.g., the beta radiation) is consumed during the treatment.

The present invention also features a radioactive composition comprising a source of beta radiation for use in a method preventing or reducing scar formation in a draining bleb associated with a foreign body in a human eye. In some embodiments, method comprises implanting foreign body within the eye of a patient, wherein the foreign body forms a bleb (e.g., a bleb in the subconjunctival space or between the conjunctiva and Tenon's capsule); and applying the beta radiation from the source of beta radiation to a target area of the eye, wherein the target area is at least a portion of the bleb. The methods herein may be effective to maintain a functioning drainage bleb. The radioactive composition (e.g., the beta radiation) is consumed during the treatment.

With reference to the methods and compositions herein, in some embodiments, the implant is for insertion between an anterior chamber of the eye and either a subconjunctival space of the eye or a space between the conjunctiva and Tenon's capsule.

With reference to the methods and compositions herein, in certain embodiments, the source of beta radiation or radioisotope provides a dose of beta radiation to the target, wherein the dose at any point on the target is within 10% of a dose at any other point on the target. In some embodiments, the radioisotope or source of beta radiation is from 4 to 15 mm in diameter.

In some embodiments, the MIGS implant is a flow controlled drainage device. In some embodiments, the MIGS implant is an implant in the eye that creates a bleb.

In some embodiments, the radioisotope or source of beta radiation is attached to an applicator (e.g., see FIG. 3, see FIG. 5A). The radioisotope or source of beta radiation may be removably attached to the applicator. The radioisotope or source of beta radiation may be fixedly attached to the applicator. In certain embodiments, the applicator comprises a handle and a distal portion and a cavity or attachment site for the source of beta radiation or radioisotope. In some embodiments, the applicator further comprises a removable cap for temporarily shielding the source of beta radiation or radioisotope. The cap may be disposable. In some embodiments, the cap is reusable.

With reference to the methods and compositions herein, in some embodiments, the target is an entire bleb. In some embodiments, the portion of the bleb that is the target is a perimeter of the bleb. In some embodiments, the portion of the bleb that is the target is a perimeter of the bleb and a portion of the bleb between a center and the perimeter. In some embodiments, the target area surrounds an end of the MIGS implant.

The present invention also features a method of inhibiting or reducing fibrogenesis and inflammation in a bleb of an eye being treated for glaucoma. The present invention also features a method of maintaining a functioning drainage bleb in the eye of a patient being treated for glaucoma. The present invention also features a method of enhancing function of a MIGS implant. The present invention also features a method of treating glaucoma. The present invention also features a method of reducing intraocular pressure (IOP) in an eye.

The present invention also features a method of inhibiting or reducing fibrogenesis and inflammation in a bleb associated with a foreign body in an eye.

With reference to the methods above, in some embodiments, the method comprises applying a radioisotope that emits beta radiation to a target of the eye, wherein the target is at least a portion of a bleb in the subconjunctival space of the eye or in a space between the conjunctiva and Tenon's capsule formed by a MIGS implant. In some embodiments, the method comprises applying a source of beta radiation to a target of the eye, wherein the target is at least a portion of a bleb in the subconjunctival space of the eye or in a space between the conjunctiva and Tenon's capsule formed by a MIGS implant. In some embodiments, the method comprises implanting a MIGS implant within the eye, wherein the implant is inserted trans-sclerally and causes formation of a bleb in the subconjunctival space of the eye or in a space between the conjunctiva and Tenon's capsule; and applying a radioisotope that emits beta radiation to a target of the eye, wherein the target is at least a portion of the bleb. In some embodiments, the method comprises implanting a MIGS implant within the eye, wherein the implant is inserted trans-sclerally and causes formation of a bleb in the subconjunctival space of the eye or in a space between the conjunctiva and Tenon's capsule; and applying a source of beta radiation to a target of the eye, wherein the target is at least a portion of the bleb.

With reference to the methods above, in some embodiments, the beta radiation causes cell cycle arrest in fibroblasts on the Tenon's capsule to inhibit or reduce the fibrotic process and inflammation that leads to bleb failure. In some embodiments, the beta radiation reduces or inhibits a fibrotic process and inflammation that causes bleb failure. In some embodiments, the method is effective to maintain the drainage function of the bleb. In some embodiments, the beta radiation is effective for maintaining function of the bleb to allow the MIGS implant to drain aqueous humor from the anterior chamber of the eye. In some embodiments, the method is effective for reducing intraocular pressure (IOP).

The present invention also features a method of treating glaucoma, wherein a MIGS implant is inserted trans-sclerally and causes formation of a bleb in the subconjunctival space of the eye or in a space between the conjunctiva and Tenon's capsule. The present invention also features a method of lowering intraocular pressure (IOP), wherein a MIGS implant is inserted trans-sclerally and causes formation of a bleb in the subconjunctival space of the eye or in a space between the conjunctiva and Tenon's capsule. The present invention also features a method of inhibiting or reducing fibrogenesis and inflammation in a bleb of an eye being treated for glaucoma, wherein a MIGS implant is inserted trans-sclerally and causes formation of a bleb in the subconjunctival space of the eye or in a space between the conjunctiva and Tenon's capsule. The present invention also features a method of maintaining a functioning drainage bleb in the eye of a patient being treated for glaucoma, wherein a MIGS implant is inserted trans-sclerally and causes formation of a bleb in the subconjunctival space of the eye or in a space between the conjunctiva and Tenon's capsule. The present invention also features a method of enhancing function of a MIGS implant, wherein the MIGS implant is inserted trans-sclerally and causes formation of a bleb in the subconjunctival space of the eye or in a space between the conjunctiva and Tenon's capsule.

With reference to the methods above, in some embodiments, the method comprises applying a radioisotope that emits beta radiation to a target area of the eye, wherein the target area is at least a portion of the bleb. In some embodiments, the method comprises applying a source of beta radiation to a target area of the eye, wherein the target area is at least a portion of the bleb.

With reference to the methods above, in some embodiments, the beta radiation causes cell cycle arrest in fibroblasts on the Tenon's capsule to inhibit or reduce the fibrotic process and inflammation that leads to bleb failure. In some embodiments, the beta radiation reduces or inhibits a fibrotic process and inflammation that causes bleb failure. In some embodiments, the method is effective to maintain the drainage function of the bleb. In some embodiments, the beta radiation is effective for maintaining function of the bleb to allow the MIGS implant to drain aqueous humor from the anterior chamber of the eye. In some embodiments, the method is effective for reducing intraocular pressure (IOP).

The present invention also features a method of reducing inflammation in an eye having a foreign body therein, the foreign body being a Minimally Invasive Glaucoma Surgery (MIGS) implant inserted between an anterior chamber of the eye and a subconjunctival space of the eye or between the anterior chamber of the eye and a space between the conjunctiva and Tenon's capsule, wherein the implant causes formation of a bleb for draining aqueous humor. In some embodiments, the method comprises applying beta radiation (e.g., applying a source of beta radiation, applying a radioisotope that emits beta radiation) to a target area of the eye, wherein the target area is at least a portion of the bleb; wherein the beta radiation is effective for reducing inflammation caused by the presence of the foreign body.

The present invention also features a method for preparing an applicator for emitting beta radiation. In some embodiments, the method comprises inserting a radioisotope that emits beta radiation (or source of beta radiation, etc.) into a cavity in an applicator, wherein the applicator comprises a handle and a distal portion with the cavity, wherein the radioisotope (or source of beta radiation, etc.) is constructed to provide a radiation dose to the target wherein a dose at any point on the target is within 10% of a dose at any other point on the target.

With reference to the aforementioned methods, in certain embodiments, a dose of beta radiation is delivered to the target, wherein the dose at any point on the target is within 10% of a dose at any other point on the target. In some embodiments, the beta radiation source, radioisotope that emits beta radiation, or source of beta radiation comprises Strontium-90 (Sr-90), Phosphorus-32 (P-32), Ruthenium 106 (Ru-106), Yttrium 90 (Y-90), or a combination thereof. In some embodiments, the beta radiation is from a beta radiation source or radioisotope, wherein the beta radiation source or radioisotope is from 4 to 15 mm in diameter. In some embodiments, the MIGS implant is a flow controlled drainage device. In some embodiments, the MIGS implant is an implant in the eye that creates a bleb. In some embodiments, the beta radiation is from a beta radiation source or radioisotope, and the beta radiation is applied to the target using an applicator. In some embodiments, the beta radiation source or radioisotope is removably attached to the applicator. In some embodiments, the beta radiation source or radioisotope is fixedly attached to the applicator. In some embodiments, the applicator comprises a handle and a distal portion and a cavity or attachment site for the beta radiation source or radioisotope. In some embodiments, the applicator further comprises a removable cap for temporarily shielding the beta radiation source or radioisotope. In some embodiments, the cap is disposable. In some embodiments, the target is an entire bleb. In some embodiments, the portion of the bleb that is the target is a perimeter of the bleb. In some embodiments, the portion of the bleb that is the target is a perimeter of the bleb and a portion of the bleb between a center and the perimeter.

The present invention also features a kit for preventing or reducing scar formation in a draining bleb in a human eye being treated for glaucoma. The present invention also features a kit for inhibiting or reducing fibrogenesis or inflammation in a bleb of an eye being treated for glaucoma. In some embodiments, the kit comprises a beta radiation source (or radioisotope that emits beta radiation) for irradiating a target area of the eye, wherein the target area is at least a portion of the bleb; and an implant for trans-scleral insertion, wherein said implant forms the bleb in the subconjunctival space of the eye or the space between the conjunctiva and Tenon's capsule.

The present invention also features a system for preventing or reducing scar formation in a draining bleb in a human eye being treated for glaucoma. The present invention also features a system for inhibiting or reducing fibrogenesis or inflammation in a bleb of an eye being treated for glaucoma. In some embodiments, the system comprises a beta radiation source (or a radioisotope that emits beta radiation) for irradiating a target area of the eye, wherein the target area is at least a portion of the bleb; and an implant for trans-scleral insertion, wherein said implant forms the bleb in the subconjunctival space of the eye or the space between the conjunctiva and Tenon's capsule.

With reference to the kits and systems above, in some embodiments, the implant is for insertion between an anterior chamber of the eye and either a subconjunctival space of the eye or a space between the conjunctiva and Tenon's capsule. In some embodiments, the beta radiation source or radioisotope provides a dose of beta radiation to the target, wherein the dose at any point on the target is within 10% of a dose at any other point on the target. In some embodiments, the source of beta radiation (beta radiation source) or radioisotope that emits beta radiation comprises Strontium-90 (Sr-90), Phosphorus-32 (P-32), Ruthenium 106 (Ru-106), Yttrium 90 (Y-90), or a combination thereof. In some embodiments, the beta radiation source or radioisotope is from 4 to 15 mm in diameter. In some embodiments, the implant is a minimally invasive glaucoma surgery (MIGS) implant. In some embodiments, the MIGS implant is a flow controlled drainage device. In some embodiments, the MIGS implant is an implant in the eye that creates a bleb. In some embodiments, the kit or system further comprises an applicator for applying the beta radiation source or radioisotope to the target area of the eye. In some embodiments, the beta radiation source or radioisotope is removably attached to the applicator. In some embodiments, the beta radiation source or radioisotope is fixedly attached to the applicator. In some embodiments, the applicator comprises a handle and a distal portion and a cavity or attachment site for the beta radiation source or radioisotope. In some embodiments, the applicator further comprises a removable cap for temporarily shielding the beta radiation source or radioisotope. In some embodiments, the cap is disposable. In some embodiments, the target is an entire bleb. In some embodiments, the portion of the bleb that is the target is a perimeter of the bleb. In some embodiments, the portion of the bleb that is the target is a perimeter of the bleb and a portion of the bleb between a center and the perimeter.

The present invention also features a radioisotope that emits beta radiation (or source of beta radiation) for use in a method of breaking up scar tissue in an eye of a patient. The present invention also features a method of breaking up scar tissue in an eye of a patient. The present invention also features a method of removing cystic structures. The present invention also features a method of needling. With reference to the compositions and methods herein, in some embodiments, the eye has a foreign body therein, e.g., a MIGS implant, and the scar tissue is a result of the presence of the foreign body. In some embodiments, the scar issue is a result of a trabeculectomy. In some embodiments, the scar tissue is a result of an ocular injury. In some embodiments, the method comprises needling scar tissue and applying beta radiation from a radioisotope that emits beta radiation (or a source of beta radiation) to the scar tissue. The method may be effective to prevent the further accumulation of scar tissue. The application of beta radiation may be before the needling or after the needling. In some embodiments, the method further comprises applying an antimetabolite to the scar tissue.

The present invention also features a radioisotope that emits beta radiation (or source of beta radiation) for use in a method of modifying a wound healing process in an eye, e.g., to reduce or inhibit inflammation, to reduce or inhibit the formation of scar tissue, to reduce or inhibit fibrogenesis, etc. The present invention also features a method of modifying a wound healing process in an eye. In some embodiments, the method comprises applying beta radiation from a radioisotope that emits beta radiation (or a source of beta radiation) to a target area of the eye, wherein the target area is a wound. In some embodiments, the method comprises applying beta radiation from a radioisotope that emits beta radiation (or a source of beta radiation) to a target area of the eye, wherein the target area is scar tissue. The method may be effective to modify cellular signaling processes that regulate wound healing so as to reduce inflammation and reduce accumulation of scar tissue. The method may be effective to prevent the further accumulation of scar tissue.

With reference to the methods and compositions above, in some embodiments, the methods further comprise administering a drug to the eye. As a non-limiting example, the methods may further comprise administering pharmaceutical eyedrops or a liquid anti-metabolite. In various embodiments, the drug may be administered before, during, or after the surgical implantation procedure.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

The features and advantages of the present invention will become apparent from a consideration of the following detailed description presented in connection with the accompanying drawings in which:

FIG. 5A shows a drawing illustrating the positioning on the eye of a beta radiation applicator.

FIG. 5B shows a drawing illustrating the positioning on the eye of sponges soaked with MMC.

FIG. 6 shows a schematic drawing of the InnFocus MicroShunt® MIGS Implant (InnFocus, Inc., Santen Pharmaceutical Co.), an example of a flow-controlled stent, and its placement within the eye.

FIG. 12 shows a schematic view of an example of previous radiation applicators that only treat the center part of the target, thereby under-dosing the peripheral area and/or overdosing the center.

FIG. 13 shows a schematic view of an example of the optimized dose delivery used in the present invention, wherein the dose applied across the target is more uniform as compared to that shown in FIG. 12. Iterative computer simulations of output dosimetry may inform an optimized design of device.

DETAILED DESCRIPTION OF THE INVENTION

Figure 1:
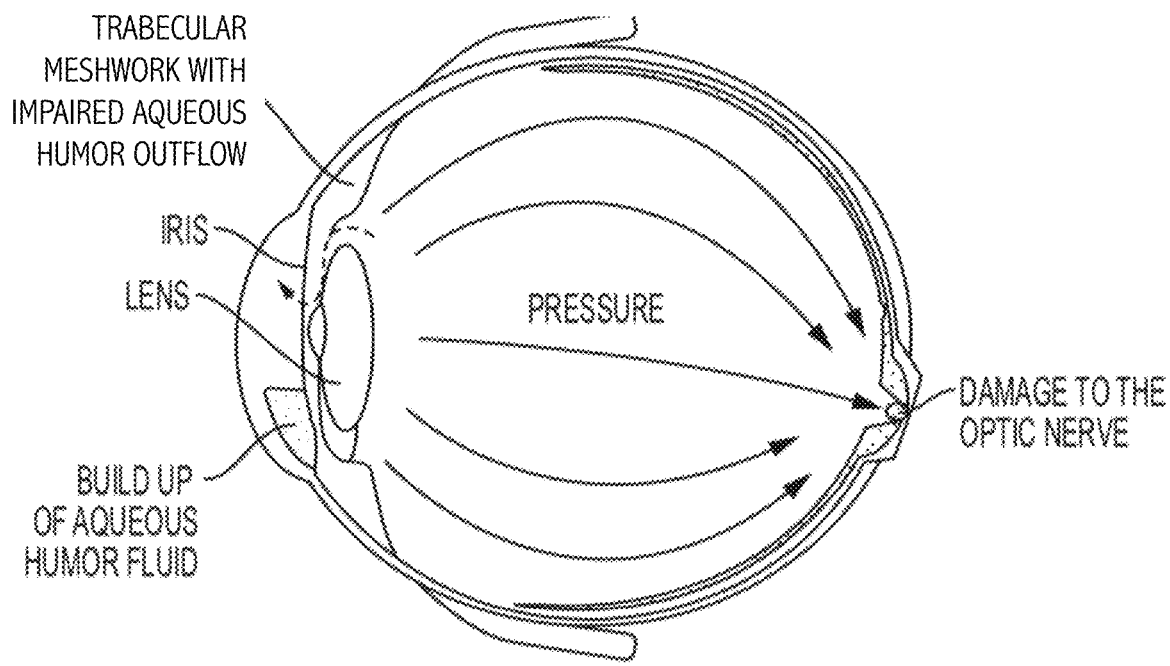
FIG. 1 shows an illustration of an eye with glaucoma.
Figure 2:
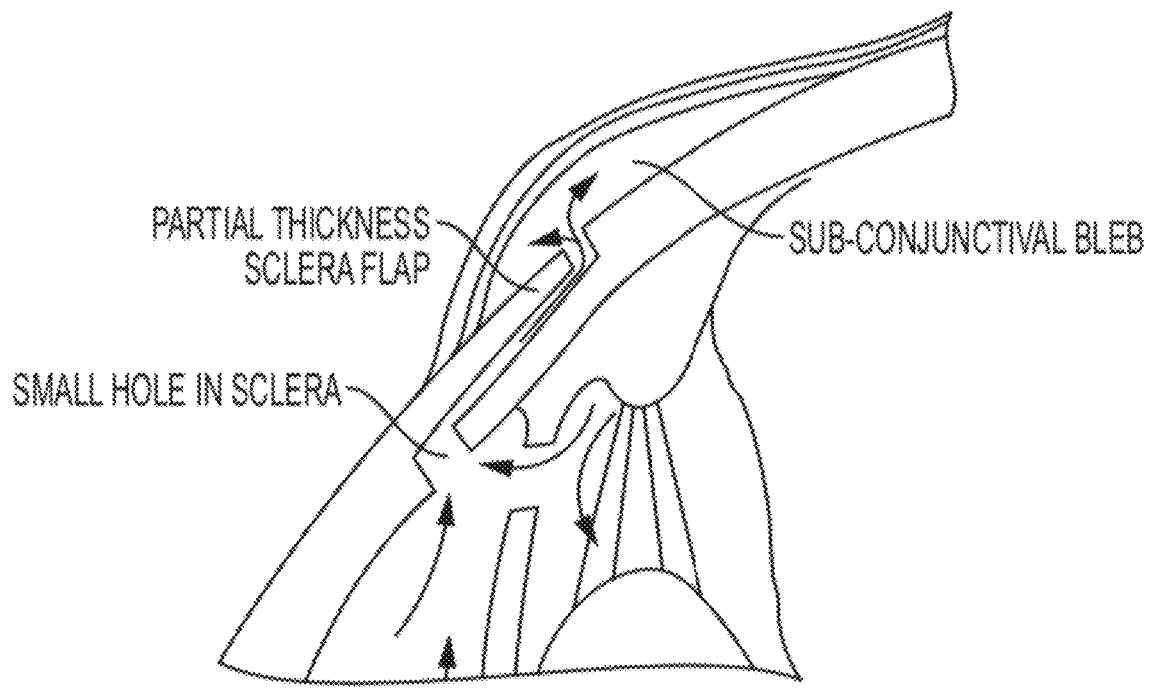
FIG. 2 shows a schematic drawing of a completed trabeculectomy featuring a partial thickness scleral flap, a small hole in the sclera and a partial iridectomy.
Figure 3:
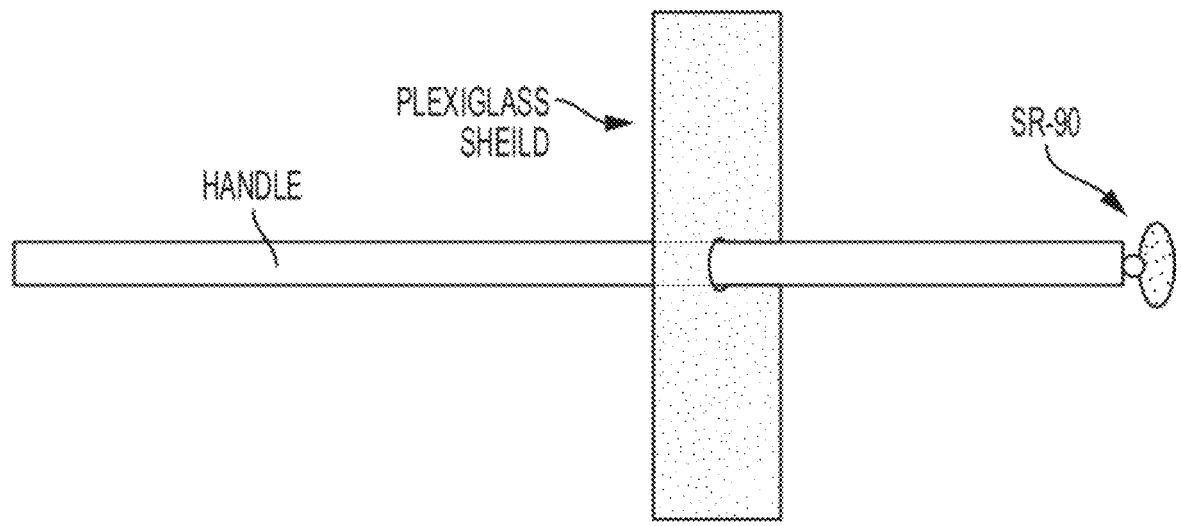
FIG. 3 shows an illustration of a Sr-90 ophthalmic beta applicator with a plexiglass shield.

The present invention provides methods and systems for maintaining a functioning drainage bleb, wherein the methods and systems feature a minimally invasive glaucoma surgery (MIGS) implant and the application of beta radiation to the drainage bleb.

One of the unique and inventive technical features of the present invention is the use of methods of treatment for glaucoma that combine MIGS implants and the application of beta radiation. Without wishing to limit the invention to any theory or mechanism, it is believed that the technical feature of the present invention advantageously provides for reduction of the IOP and formation of a healthy bleb. None of the presently known prior references or work has the unique inventive technical feature of the present invention.

As used herein, the term "functioning drainage bleb" refers to a bleb that is effective for the draining of aqueous humor from the eye to reduce the IOP of the eye to an appropriate level. For example, a functioning drainage bleb may relate to a normal IOP.

Early bleb grading systems included those proposed by Kronfeld (1969), Migdal and Hitchings (1983), and Picht and Grehn (1998). Subsequent bleb grading systems identified and incorporated a graded assessment of various bleb parameters such as vascularity, height, width, microcystic changes, encystment and diffuse/demarcated zones.

There are two recently described grading systems for clinical grading of filtering surgery blebs: the Moorfields Bleb Grading System (MBGS) and the Indiana Bleb Appearance Grading Scale (IBAGS). The MBGS built upon the system used for this tele-medicine study and expanded it to include an assessment of vascularity away from the center of the bleb and a way to represent mixed-morphology blebs. In this scheme, central area (1-5), maximal area (1-5), bleb height (1-4) and subconjunctival blood (0-1) were assessed. In addition, three areas of the bleb were graded separately for vascularity, including bleb center conjunctiva, peripheral conjunctiva and non-bleb conjunctiva. Vascularity in each area was assigned a score from 1 to 5. A study found good inter-observer agreement and clinical reproducibility in the IBAGS and MBGS (Wells A P, Ashraff N N, Hall R C, et al. Comparison of two clinical bleb grading systems. Ophthalmology 2006; 113:77-83.)

The Moorfields bleb grading system was developed as the importance of bleb appearance to outcome was realized. Blebs that develop thin avascular zones are at increased risk of leakage and late hypotony as well as sight threatening bleb related infections.

The Indiana Bleb Appearance Grading Scale is a system for classifying the morphologic slit lamp appearance of filtration blebs. The Indiana Bleb Appearance Grading Scale contains a set of photographic standards illustrating a range of filtering bleb morphology selected from the slide library of the Glaucoma Service at the Indiana University Department of Ophthalmology. These standards consist of slit lamp images for grading bleb height, extent, vascularity, and leakage with the Seidel test. For grading, the morphologic appearance of the filtration bleb is assessed relative to the standard images for the 4 parameters and scored accordingly.

For reference, a failed or failing bleb may have "restricted posterior flow with the so-called 'ring of steel'," e.g., a ring of scar tissue or fibrosis adhering the conjunctiva to the sclera at the periphery of the bleb that restricts the flow of aqueous humor (see Dhingra S, Khaw P T. The Moorfields Safer Surgery System. Middle East African Journal of Ophthalmology. 2009; 16(3):112-115). Other attributes of failed or failing blebs may include cystic appearance and/or changes in vascularization and/or scar tissue and/or thinning of the conjunctiva overlaying the bleb and/or a tense bleb and/or other observable or measurable changes as may be included in either the Indiana Bleb Appearance Grading Scale or Moorfields Bleb Grading System. Other functional determinates of failed or failing blebs or glaucoma surgery may include increased IOP, or IOP that has not decreased sufficiently.

As used herein, the term "drainage device" refers to any or a combination of the general and specific approaches for draining aqueous humor, such as the therapeutics and devices described herein, including minimally invasive glaucoma surgery (MIGS) devices and surgery, that are employed to reduce Intraocular Pressure by means of a surgical intervention with a device.

Glaucoma Drainage Procedures and Devices

Various glaucoma drainage procedures and devices, including trabeculectomy, drainage tubes, and devices used for Minimally Invasive Glaucoma Surgery (MIGS), are described below.

MIGS is a recent innovation in the surgical treatment of glaucoma developed to minimize the complications from tubes and trabeculectomy. MIGS is a term applied to the widening range of implants, devices, and techniques that seek to lower intraocular pressure with less surgical risk than the more established procedures. In most cases, conjunctiva-involving devices require a subconjunctival bleb to receive the fluid and allow for its extraocular resorption. Flow-controlled conjunctiva-involving devices typically attempt to control flow and lower IOP to normal pressure and also minimizing hypotony (too low pressure in the eye) by applying Poiseuille's law of laminar flow to create a tube that is sufficiently long and narrow to restrict and control outflow. Non-limiting examples of glaucoma drainage devices and procedures are described below. Note that the blebs formed by trabeculectomy procedures may be different from blebs formed by MIGS implants, e.g., the blebs may be placed at different locations, etc. Note that the glaucoma drainage surgeries and blebs that have scarred or are failing or have failed may be different from blebs formed at the time of the original glaucoma drainage surgery.

Trabeculectomy

Trabeculectomy is a procedure wherein a small hole is made in the sclera and is covered by a thin trap-door. Aqueous humor drains through the trap door to a bleb. In some trabeculectomy procedures, an initial pocket is created under the conjunctiva and Tenon's capsule and the wound bed is treated with mitomycin C soaked sponges using a "fornix-based" conjunctival incision at the corneoscleral junction. A partial thickness scleral flap with its base at the corneoscleral junction after cauterization of the flap area is created. Further, a window opening is created under the flap with a Kelly-punch or a Khaw Descemet Membrane Punch to remove a portion of the sclera, Schlemm's canal, and the trabecular meshwork to enter the anterior chamber. An iridectomy is done in many cases to prevent future blockage of the sclerostomy. The scleral flap is then sutured loosely back in place with several sutures. The conjunctiva is closed in a watertight fashion at the end of the procedure.

Trans-Scleral Drainage Devices

Figure 7:
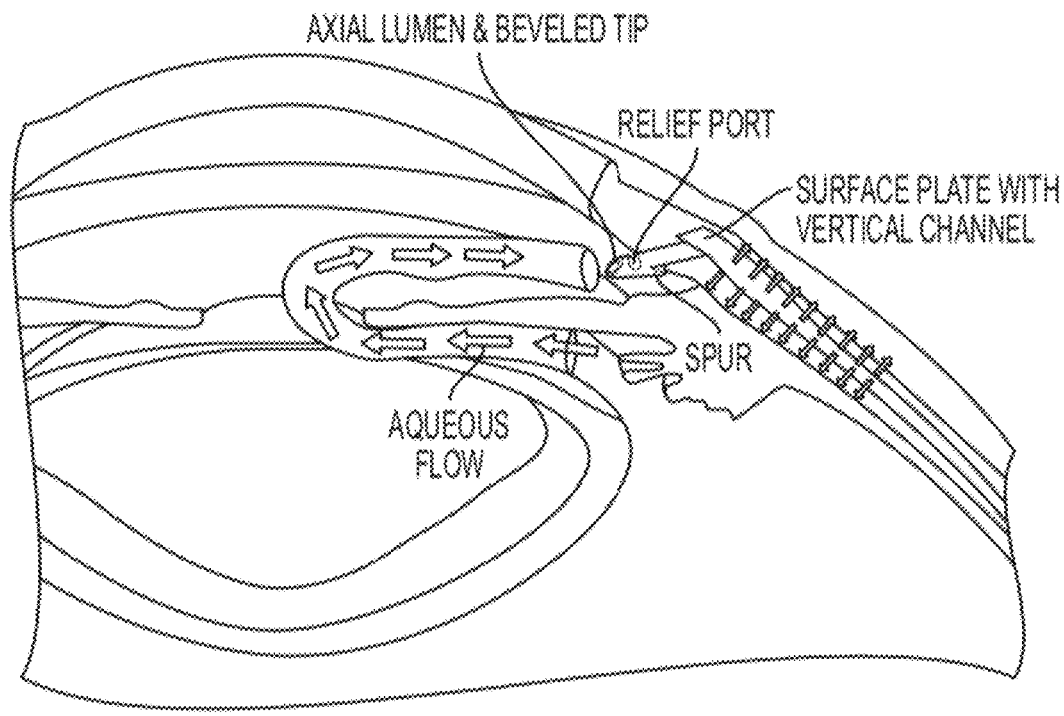
FIG. 7 shows a schematic drawing of the EX-PRESS® (Novartis AG Corporation) MIGS Implant, an example of a trans-scleral drainage device, within the eye.
Figure 8:
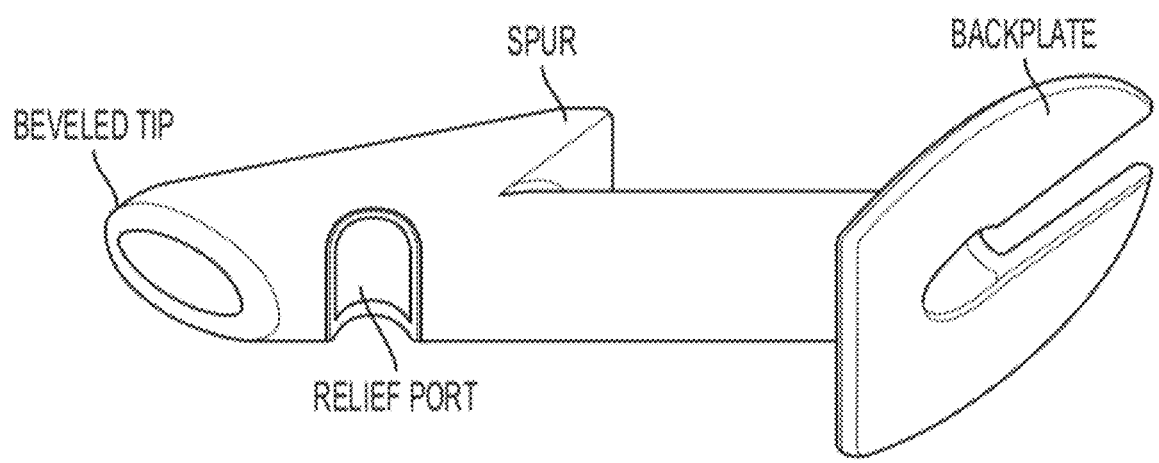
FIG. 8 shows a schematic drawing of the EX-PRESS® (Novartis AG Corporation) MIGS Implant, an example of a trans-scleral drainage device.
Figure 9A:
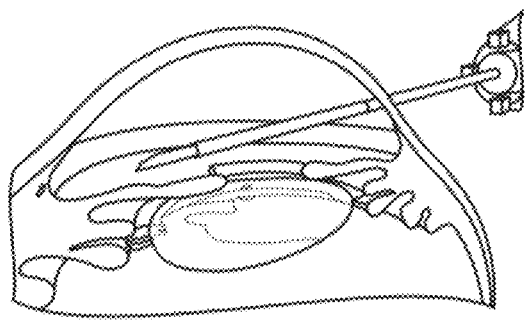
FIG. 9A shows a schematic drawing of the first step in the process of implanting the XEN® MIGS implant (AqueSys, Inc.), a flow-controlled MIGS device, within an eye.
Figure 9B:
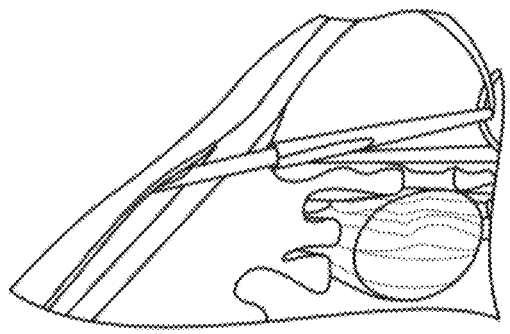
FIG. 9B shows a schematic drawing of the second step in the process of implanting the XEN® MIGS implant (AqueSys, Inc.), a flow-controlled MIGS device, within an eye.
Figure 9C:
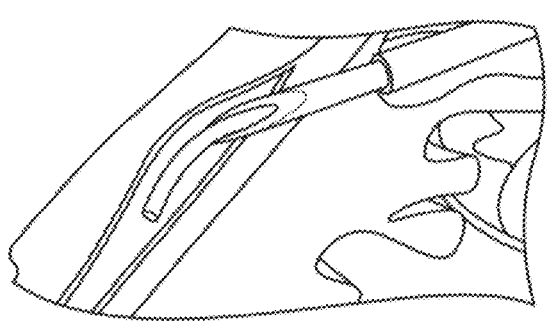
FIG. 9C shows a schematic drawing of the third step in the process of implanting the XEN® MIGS implant (AqueSys, Inc.), a flow-controlled MIGS device, within an eye.
Figure 9D:
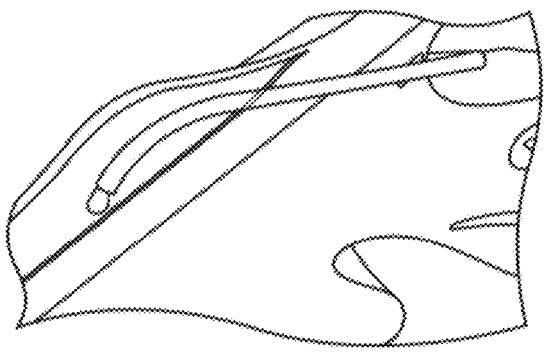
FIG. 9D shows a schematic drawing of the final step in the process of implanting the XEN® MIGS implant (AqueSys, Inc.), a flow-controlled MIGS device, within an eye.

Trans-scleral drainage devices shunt aqueous humor from the anterior chamber to a subconjunctival reservoir. As an example of a trans-scleral drainage device, the EX-PRESS® (Novartis AG Corporation) Glaucoma Filtration Device channels aqueous humor through a secure lumen (e.g., 50 µm or 200 µm) to a half-thickness scleral flap, creating a subconjunctival filtration bleb (see FIG. 7, FIG. 8). The device's lumen provides a standardized opening for aqueous humor flow while also providing some resistance, which appears to add further stability to the anterior chamber during surgery and the early post-op period.

More specifically, the surgical technique entails the implantation of a shunt under a scleral flap to drain aqueous humor from the anterior chamber into the intrascleral space. After proper eye positioning and anesthesia, a conjunctival peritomy is fashioned superiorly and dissected back. The scleral bed is cauterized for hemostasis, followed by the creation of a triangular scleral flap with a base approximately 3 mm in width.

Next, the scleral flap is brought forward into clear cornea. Using a cellulose ophthalmic sponge, mitomycin-C is placed onto the scleral bed for approximately three minutes, removed, then irrigated with balanced salt solution (BSS). A 25-gauge needle is used to make a scleral tunnel incision into the anterior chamber parallel to the iris plane.

The shunt is then inserted and fashioned into this opening, flush with the sclera. Aqueous flow is tested for adequacy, then the flap is brought down and closed with three interrupted sutures that are tied and buried. BSS is instilled into the anterior chamber to evaluate outflow potential through the flap. Lastly, the conjunctiva is pulled forward and peritomy closed superiorly.

Flow Controlled Stents

Some MIGS-associated devices control flow of the aqueous humor. One example of a flow-controlled device is the XEN® gel stent (AqueSys, Inc.), which is a gelatin and glutaraldehyde tube preloaded in a disposable injector and implanted using an ab interno approach. For example, the surgeon inserts the injector through a clear cornea incision and tunnels through the sclera at or anterior to Schlemm's canal to deploy the distal portion of the stent within the subconjunctival space. This creates a pathway for aqueous to flow from the anterior chamber to the subconjunctival space, forming a bleb.

Another flow-controlled stent is the InnFocus MicroShunt® (InnFocus, Inc., Santen Pharmaceutical Co.) (see FIG. 6). The InnFocus MicroShunt® (InnFocus, Inc., Santen Pharmaceutical Co.) flow-controlled stent is a 8.5 mm long implant made of poly(styrene-block-isobutylene-block-styrene). The surgeon inserts this device into the anterior chamber through an ab externo approach, creating a bleb in the subconjunctival space.

Additional MIGS-Associated Devices

Other MIGS devices include microshunts to Schlemm's Canal, suprachoroidal devices, and devices for trabeculotomy devices.

Examples of microshunts to Schlemm's Canal include iStent® (Glaukos Corporation) and Hydrus® (Ivantis, Inc.). iStent® (Glaukos Corporation) is an L-shaped microstent inserted using an ab interno approach into the lumen into Schlemm's canal. The neck extends into the anterior chamber to create a direct connection from the anterior chamber to Schlemm's canal. By bypassing the trabecular meshwork (TM), the stent is designed to increase aqueous outflow. Hydrus® (Ivantis, Inc.), an example of a microshunt to Schlemm's Canal, is an 8 mm device used to improve aqueous outflow by providing a direct connection between the anterior chamber and Schlemm's canal. It creates a three clock-hour scaffolding of the canal, and three windows on the anterior face of the device stretch the TM and increase aqueous outflow.

Examples of suprachoroidal devices include CyPass® (Novartis AG Corporation), Solx® gold shunt (Solx Inc.), and iStent Supra (Glaukos Corporation). CyPass® (Novartis AG Corporation) is an example of an ab interno suprachoroidal shunt made of brown polyimide material. It has a 0.3 mm lumen and comes preloaded in a curved inserter. The surgeon inserts the device through a temporal clear corneal incision into the nasal angle posterior to the scleral spur, with the distal portion of the device embedded in the suprachoroidal space. The shunt diverts aqueous from the anterior chamber into the suprachoroidal space using the uveoscleral outflow system. Aqueous not only flows through the lumen of the stent, but also through fenestrations in the distal portion of the device. Solx® (Solx, Inc.), an example of a suprachoroidal device, is a gold shunt made of 24-carat gold. This flat stent is inserted using an ab externo approach through a scleral incision in any quadrant of the eye. The anterior portion of the stent is placed 1 mm into the anterior chamber with the posterior end of the stent in the suprachoroidal space. iStent Supra (Glaukos Corporation) is a suprachoroidal shunt comprised of polyethersulfone and titanium. The placement and mechanism of action are identical to the CyPass® (Novartis AG Corporation) suprachoroidal stent.

An example of a trabeculotomy device includes the Trabectome® (NeoMedix) electrocautery device. A surgeon inserts the Trabectome® (NeoMedix) trabeculectomy device through a temporal clear corneal incision and directs it to the nasal portion of the angle. The TM and interior wall of Schlemm's canal are removed via cauterization anywhere from 90° to 180°. Aspiration and irrigation ports on the tip of the device maintain homeostasis during the procedure.

Valves

Valves, such as the Baerveldt® implant (Johnson & Johnson), the Ahmed® glaucoma valve (New World Medical), the Krupin-Denver eye valve to disc implant (E. Benson Hood Laboratories), and the Molteno® and Molteno3® drainage devices (Nova Eye Medical), are also used as glaucoma drainage devices. Instead of using a natural bleb, these devices use a synthetic reservoir (or plate), which is implanted under the conjunctiva to allow flow of aqueous fluid.

As an example, the placement procedure for the Ahmed® (New World Medical) valve involves: raising a fornix-based flap of the conjunctiva and Tenon's capsule; placing a corneal or episcleral traction suture; performing posterior dissection with Westcott or Stevens scissors to create a pocket where the implant's plate will be located; securing the plate with sutures behind the limbus; cutting the tube tip obliquely to protect the tube lumen from the iris; entering into the anterior chamber with a needle tract; positioning the tube in the anterior chamber anterior to the iris and away from the corneal endothelium; securing a patch graft with sutures over the exposed portion of the tube; suturing conjunctiva; and reforming the anterior chamber with balanced salt solution or viscoelastic through the paracentesis tract. When using the Baerveldt® (Johnson & Johnson) valve, the surgical procedure requires some modifications compared to the procedure for the Ahmed® (New World Medical) valve. For example, the lateral and superior rectus muscles are isolated with muscle hooks and the wings of the plate are placed under each muscle belly. Since the Baerveldt® (Johnson & Johnson) valve is a nonrestrictive device, maneuvers are performed in order to avoid postoperative hypotony.

The success of these devices depends on the formation and maintenance of a permeable capsule around the episcleral plate, through which the aqueous humor percolates into surrounding tissues by simple diffusion. The capsule around the shunt plate provides the primary resistance to aqueous humor outflow through the drainage device. As a result, an important factor in determining the long-term intraocular pressure control is the permeability of the capsule surrounding the plate. Note that progressive capsular fibrosis around the implant and relative impermeability of the shunt capsule in many cases results in clinical failure, necessitating further medical or surgical management. One failure mechanism is hypertrophy or thickening of the conjunctiva.

The use of anti-metabolites with some success in trabeculectomy led to interest in using these agents with glaucoma drainage devices. However, two retrospective studies reported no benefit of intraoperative use of mitomycin C with Baerveldt® (Johnson & Johnson) valves. Two prospective randomized trials studied the effectiveness of intraoperative use of mitomycin C with Molteno® valves (Nova Eye Medical) and AGV implantation, and neither trial demonstrated higher success rates with intraoperative mitomycin C in terms of final IOP, visual acuity, and number of antiglaucoma medications required postoperatively. As a result of these investigations, antifibrosis agents are not currently used with glaucoma drainage devices.

Although MMC was not able to prevent hypertrophy of the conjunctiva, beta radiation may succeed where MMC failed. Without wishing to limit the invention to any particular theory or mechanism, it is believed that use of beta radiation may reduce or prevent conjunctival hypertrophy, thereby providing higher success rates for valves than the use of liquid anti-metabolites or the absence of an antifibrosis agent.

Camras Shunt

The Camras Shunt is a device currently under development for reducing intraocular pressure and includes first and second resilient flexible tubes connected together to permit fluid flow therethrough. The first tube has one end inserted within the anterior chamber of the eye to drain fluid therefrom and extends through an aperture in the conjunctival layer. The second tube is connected to the external end of the first tube, and has an operable valve at the free end thereof that opens when subjected to a predetermined fluid pressure to thereby reduce the intraocular pressure of the eye. A filter is mounted within the second tube to prevent bacteria from entering the anterior chamber of the eye while permitting replacement of the filter.

Custom Device by New World Medical

A custom device by New World Medical is described in the Digital Journal of Ophthalmology (Dohlman et al., 2005, Digital Journal of Ophthalmology 11(2)). This valve shunt device was implanted to divert the aqueous humor to the lower lid fornix, thereby wetting the eye in a patient with severe dry eye.

The surgery consisted of implanting a valve shunt that had been custom manufactured by New World Medical, Inc. (Rancho Cucamonga, Calif.). The shunt consists of a proximal fine tube of silicone to be inserted to the anterior chamber. It connects to a valve similar to that of a standard Ahmed S-2 valve shunt, made for an opening pressure of 10-12 mm Hg. The custom shunt did not have a plate;

instead, a silicone rubber housing enclosed the valve. A distal tube emerges from the side of this housing to be drawn up to the lower lid fornix.

The proximal tube to the anterior chamber was inserted beneath a half-depth scleral flap, entering into the anterior chamber through a needle track of the limbus. The tube extended into the anterior chamber and was positioned anterior to the iris. The valve housing was sutured to the sclera in the lower nasal quadrant in a manner similar to the attachment of a standard S-2 shunt plate. The distal tube was tied to a suture and the needle was passed temporally under the conjunctiva to about midpoint of the fornix where it was exited upwards, and the tube was pulled through. The tube was cut so that it was allowed to lie flat in the fornix, extending for about one centimeter. Two sutures were placed to temporarily keep the tube flat at the bottom of the fornix. Aqueous humor could immediately be seen trickling out of the tube opening.

For the purposes of the invention, other surgical innovations and/or devices in addition to those described above may be included in the scope of the invention and described and labeled as MIGS. For example, techniques and devices that may alternatively be described as Moderately Invasive Glaucoma Surgery or Augmented Incisional Surgery is also included in the present invention.

Isotopes and Radioactivity

The US Nuclear Regulatory Commission (USNRC) (https://www.nrc.gov/about-nrc/radiation/health-effects/measuring-radiation.html) defines radioactivity as "the amount of ionizing radiation released by a material. Whether it emits alpha or beta particles, gamma rays, x-rays, or neutrons, a quantity of radioactive material is expressed in terms of its radioactivity (or simply its activity), which represents how many atoms in the material decay in a given time period. The units of measure for radioactivity are the curie (Ci) and becquerel (Bq)." Activity in a radioactive-decay process is defined as the number of disintegrations per second, or the number of unstable atomic nuclei that decay per second in a given sample. Activity is expressed in the International System of Units by the becquerel (abbreviated Bq), which is exactly equal to one disintegration per second. Another unit that may be used is the Curie, wherein one curie is approximately the activity of 1 gram of radium and equals (exactly) $3.7 \times 10^{10}$ becquerel. The specific activity of radionuclides is relevant when it comes to select them for production for therapeutic pharmaceuticals.

By the USNRC definition, absorbed dose is defined as the amount of radiation absorbed, e.g., the amount of energy that radioactive sources deposit in materials through which they pass or the concentration of energy deposited in tissue as a result of an exposure to ionizing radiation. The absorbed dose is equal to the radiation exposure (ions or Ci/kg) of the radiation beam multiplied by the ionization energy of the medium to be ionized. Typically, the units for absorbed dose are the radiation absorbed dose (rad) and gray (Gy). Gy is a unit of ionizing radiation dose defined as the absorption of one joule of radiation energy per kilogram of matter. The rad has generally been replaced by the Gy in SI derived units. 1 Gy is equivalent to 100 rad.

Radionuclide generators are devices that produce a useful short-lived medical radionuclide (known as "daughter" products) from the radioactive transformation of a long-lived radionuclide (called a "parent"). By having a supply of parent on hand at a facility, the daughter is continually generated on site. The generator permits ready separation of the daughter radionuclide from the parent. One of the most widely used generator devices (often referred as a "cow") is the technetium 99 generator. It allows the extraction of the metastable isotope 99mTc of technetium from a source of decaying molybdenum-99. 99Mo has a half-life of 66 hours and can be easily transported over long distances to hospitals where its decay product technetium-99m (with a half-life of only 6 hours, inconvenient for transport) is extracted and used for a variety of nuclear medicine procedures, where its short half-life is very useful.

Generators can also be constructed for supply of other daughter radioisotopes. Ruthenium 106 (Ru-106) is a commercially available radioisotope with a half-life of 668-373 days, making it a good candidate for a parent isotope in a cow or generator. The decay of Ru-106 to rhodium-106 (Rh-106) produces only a low energy beta of 39 Key that is not useful for therapy. However, Rh-106 has an energetic beta decay useful for brachytherapy: Rh-106 has a half-life of 30 seconds and decays by beta emission to palladium 106 (Pd-106) with a maximum decay energy of 3.541 Mev and an average energy of 96.9 Key. As an example, in some embodiments, the present invention features a device loaded from a Ruthenium-106 cow with an activity of rhodium-106 providing for the full prescribed dose. The device can be applied to the target volume to deliver the full activity of its contents. For example, the device may be placed over the target lesion for 10 half-lives (300 seconds), delivering all its radioactive energy and consuming the rhodium-106, depleting it to palladium.

In some embodiments, the present invention features the use of Ru-106 in secular equilibrium with Rh-106. Ru-106 decays by beta radiation to Rh-106. The two isotopes are in secular equilibrium with the decay rate of the combined source controlled by the Ru-106 parent but with the therapeutic beta radiations emanating from the daughter Rh-106.

Yttrium-90 is commercially available from Strontium-90 cows. As another example, in some embodiments, the present invention features the use of Yttrium-90 with a half-life of 64 hours. Y-90 decays to Zirconium 90 (Zr-90), a stable isotope, along three different routes via beta emission, wherein 99.985% of the time it decays with a maximum beta particle energy of 2.2801 MeV and a mean beta particle energy of 0.9337 MeV, or approximately or 1.5×10-13 joules. The other minor decay paths produce additional low energy gamma-rays, and electrons. Compared to the dominant path, the radiation doses from these paths are clinically negligible.

Figure 4:
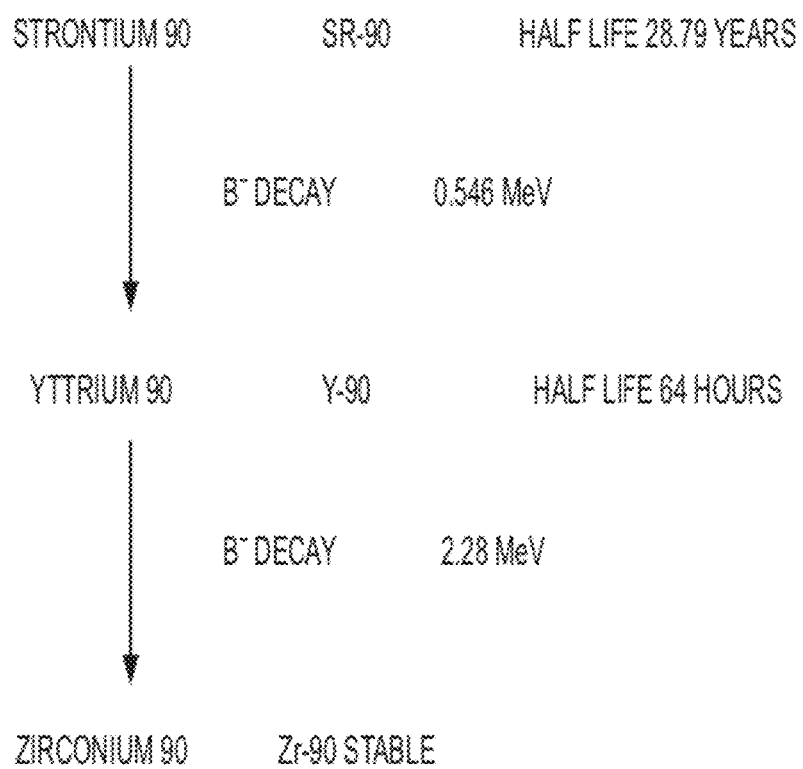
FIG. 4 shows a schematic illustration of the radioactive decay of Strontium 90 and the resulting beta emission.

Currently, strontium-90 is also commercially available. As another example, in some embodiments, the present invention features the use of Strontium 90 (Sr-90) in secular equilibrium with Yttrium 90 (Y-90). Strontium 90 (Sr-90) decays by beta radiation to Yttrium 90 (Y-90) (see FIG. 4). The parent Sr-90 isotope has a half-life of 28.79 years. The daughter Y-90 isotope has a half-life of 64.0 hours. The two isotopes are in secular equilibrium with the decay rate of the combined source controlled by the Sr-90 parent but with the therapeutic beta radiations emanating from the daughter Y-90 with maximum energy of 2.28 MeV and an average energy of 934 keV.

Figure 10:
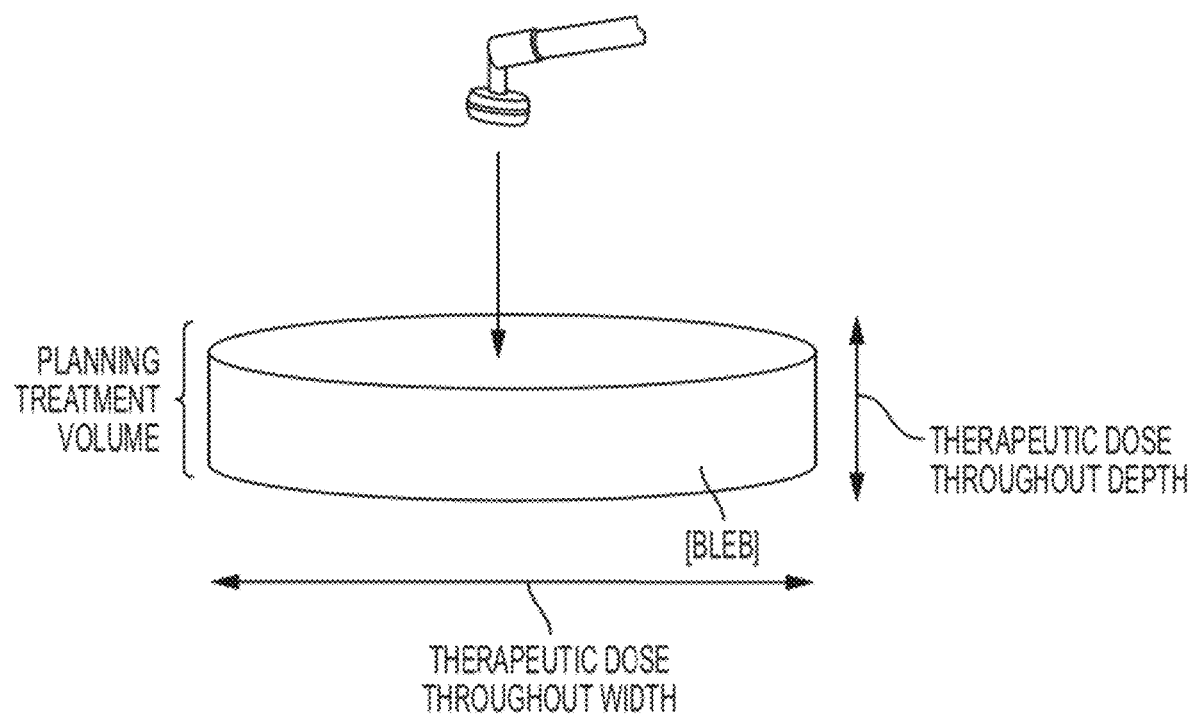
FIG. 10 shows a schematic view of the planning treatment volume of the bleb, wherein a therapeutic dose is applied throughout the width and depth of the target.
Figure 11:
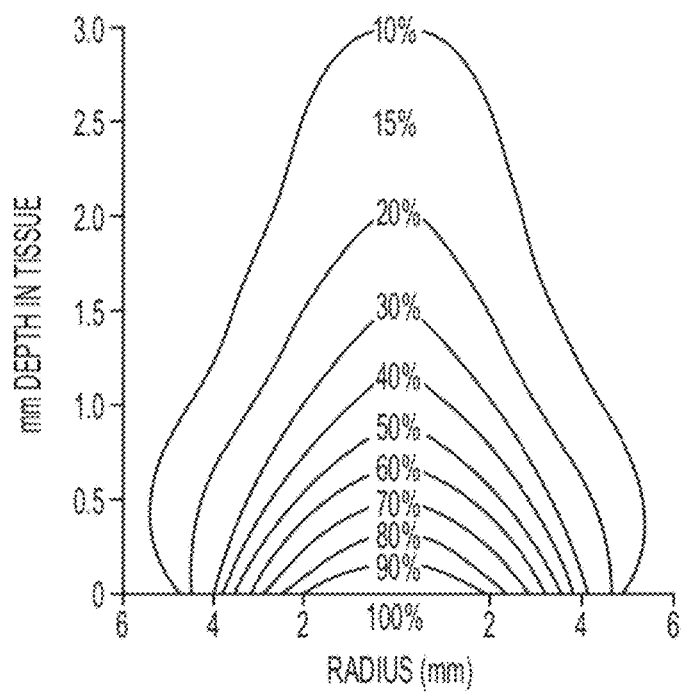
FIG. 11 shows a series of isodose curves of a Sr-90 beta applicator and the penetration depth of the radiation in tissue.
Figure 14:
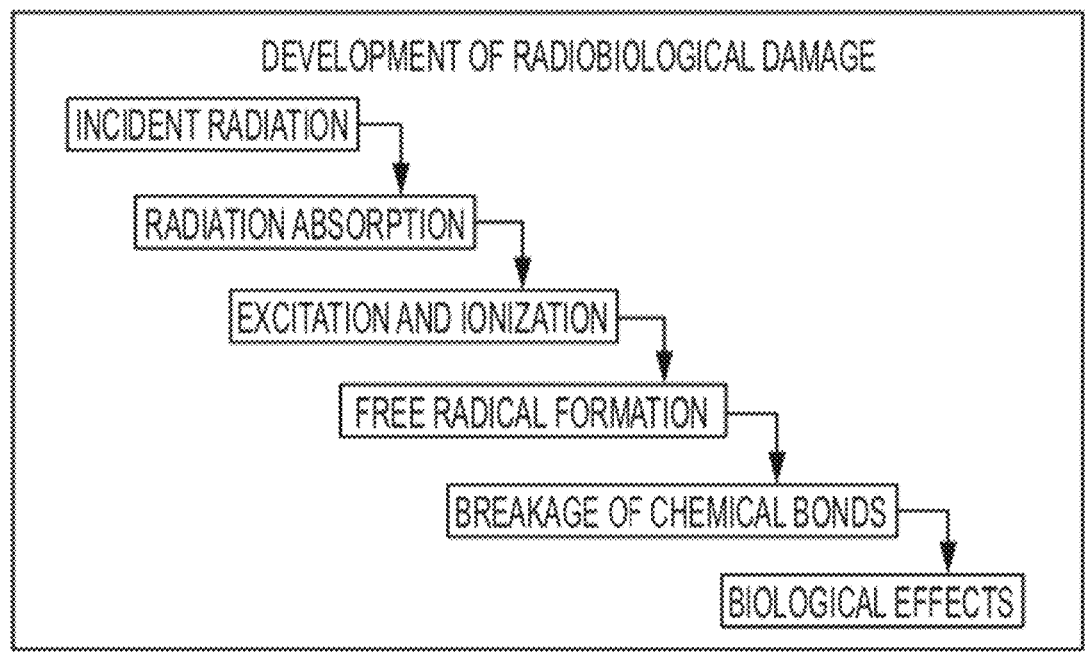
FIG. 14 shows a schematic illustrating the development of radiobiological damage.
Figure 15:
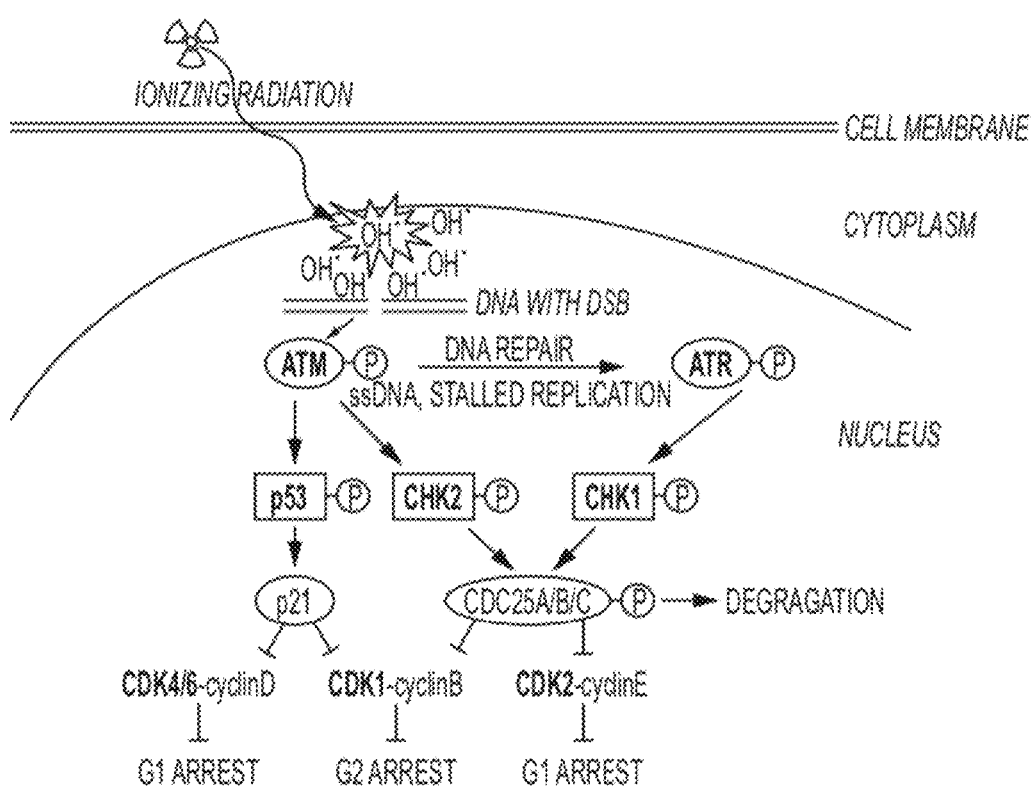
FIG. 15 shows a schematic of the induction of cell cycle arrest after irradiation. The hydroxyl radical is the most important aqueous radical induced by ionizing radiation (symbolized by the sinuous arrow and the trefoil) affecting the integrity of DNA (parallel lines) by induction of double strand breaks (DSB, gap in DNA). Subsequently, the ATM (ataxia-telangiectasia mutated) kinase is activated by phosphorylation (encircled P) and, in turn, phosphorylates p53. ATR (ataxia-telangiectasia and RAD3-related) is activated by single-stranded DNA and stalled replication forks arising from the repair process. Activated p53 acts as a transcription factor and causes the expression of the cyclin-dependent kinase (CDK) inhibitor p21, which induces cell cycle arrest during the G1 and G2 phases. On the other hand, activation of CHK1 and CHK2 (checkpoint kinase-1 and -2) leads to phosphorylation of the three CDC25 (cell division cycle 25) isoforms, resulting in its degradation. As a consequence, CDC25 no longer activates CDK2 or CDK1 (cyclin-dependent kinase), and thus, the cell cycle is stopped in the G1 or G2 phase, respectively. Arrows symbolize activation; bar-headed lines symbolize inhibition. See Maier, 2016, Int. J. Mol. Sci. 17, 102; doi:10.3390/ijms17010102
Figure 16:
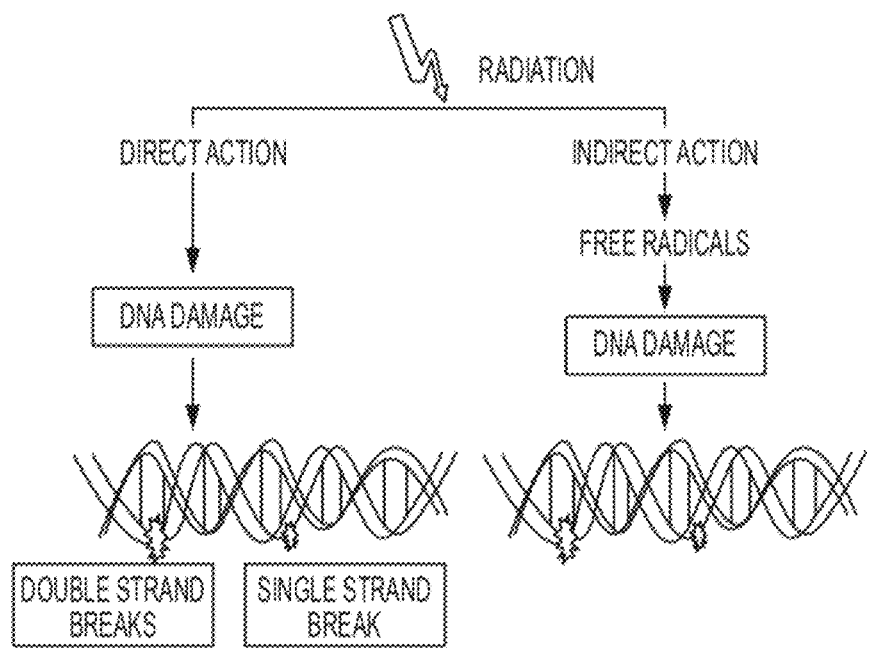
FIG. 16 shows a schematic view of how radiation can act in two ways: (1) It induces ionizations directly on the cellular molecules and causes damage; and (2) it can act indirectly by producing free radicals that are derived from the ionization or excitation of water in the cells.
Figure 17:
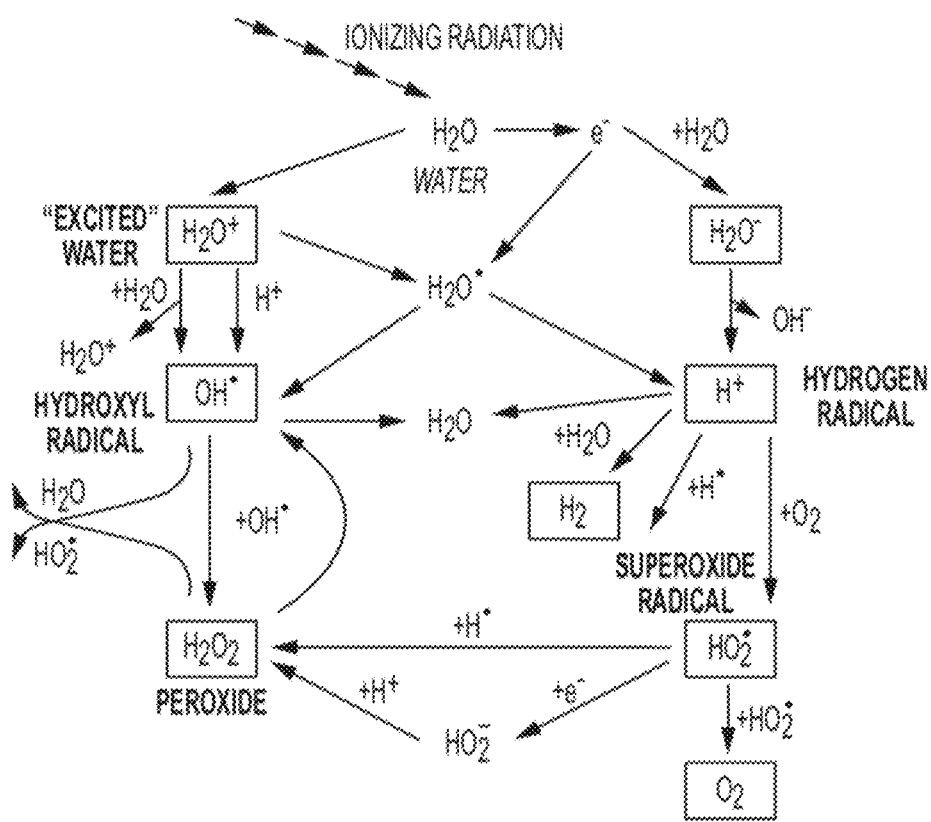
FIG. 17 shows a schematic of the radiolysis of intracellular water.

The Planning Target Volume (PTV) or Planning Treatment Volume (PTV) is a geometrical concept introduced for radiation treatment planning (see also FIG. 10, FIG. 11). The PTV is used to ensure that the prescribed dose is actually delivered to all parts of the target tissue. Without limiting the invention to any particular surgical practice, a medical journal article details the surgical creation of the bleb in which "the surgeon dissects backward with Westcott scissors to make a pocket approximately 10 to 15 mm posteriorly and sufficiently wide to accommodate the antimetabolite sponges". In this example, the surgeon opened the potential space under the conjunctiva and Tenon's capsule creating an approximately 10 to 15 mm diameter bleb site. As an example, it would follow that the Target Volume could be defined as a disk of diameter 15 mm and depth of 0.3 mm, containing the conjunctiva and Tenon's capsule tissue.

For example, a prescription dose of brachytherapy of 10 Gray (1000cGy) is 10 joules/kg absorbed dose throughout the Target Volume. Measurements have suggested a model Sr-90/Y-90 RBS with Activity of 1.48 GBq produces a surface dose rate of approximately 0.20 Gy per second. To deliver a dose of 10 Gy to the Target Volume would require an irradiation time of 50 seconds. The number of nuclei that decay during this 50 second treatment would be $1.48 \times 10^9$ Bq (disintegrations per second)×50 seconds=$7.4 \times 10^{10}$.

Biological Effects of Radiation

The biological effectiveness of radiation depends on the linear energy transfer (LET), total dose, fractionation rate, and radiosensitivity of the targeted cells or tissues. As radiation interacts with matter, it loses its energy through interactions with atoms in its direct path. In radiation therapy, LET is defined as the average amount of energy lost per defined distance in tissue, as in the energy deposited into a handful of cells. LET occurs at different rates in different tissues, and quantification of LET in cellular systems is an important component of determining correct dosage in radiology. Low LET radiations are X-rays, gamma rays and beta particles.

Referring to FIG. 14, FIG. 15, FIG. 16, and FIG. 17, radiation induced ionizations can act directly on the cellular molecules and cause damage, such as DNA damage. Radiation induced ionizations also can act indirectly, producing free radicals that are derived from the ionization or excitation of the water component of the cell. Exposure of cells to ionizing radiation induces high-energy radiolysis of $H_2O$ water molecules into H+ and OH— radicals. These radicals are themselves chemically reactive, and in turn recombine to produce a series of highly reactive combinations such as superoxide ($O_2^-$) and peroxide ($H_2O_2$) that produce oxidative damage to molecules, such as DNA, within the cell. Ionizing radiation-induced DNA breaks represent one of the dominant mechanisms of action of beta brachytherapy.

Multiple pathways are involved in the cell after its exposure to ionizing radiation. In the cellular response to radiation, several sensors detect the induced DNA damage and trigger signal transduction pathways. The activation of several signal transduction pathways by ionizing radiation results in altered expression of a series of target genes.

The promoters or enhancers of these genes may contain binding sites for one or more transcription factors, and a specific transcription factor can influence the transcription of multiple genes. The transcription factors p53, nuclear factor κB (NF-κB), the specificity protein 1 (SP1)-related retinoblastoma control proteins (RCPs), two p53-dependent genes, GADD45 and CDKN1A, and genes associated with the NER pathway (e.g., XPC) are typically upregulated by ionizing radiation exposure. Interestingly, NF-κB activation has been shown to strongly depend on charged particles' LET, with a maximal activation in the LET range of 90-300 keV/μm.

Importantly, the transcribed subset of target genes is critical for the decision between resuming normal function after cell-cycle arrest and DNA repair, entering senescence, or proceeding through apoptosis in cases of severe DNA damage.

Arrest of the cell cycle is an important part of DNA damage response, facilitating DNA repair and maintenance of genomic stability. Regulators of cell cycle arrest are activated by phosphorylation by ataxia telangiectasia mutated (ATM) and ATR. For example, p53 has a short half-life and is stabilized in response to a variety of cellular stresses after phosphorylation by ATM. After exposure to ionizing radiation, phosphorylation of the serine residues 15 and 20 on p53 by checkpoint kinase 2 (CHK2) reduces its binding to MDM2, which in its bound state targets p53 for degradation by the proteasome pathway. Thus, dissociation of p53 from MDM2 prolongs the half-life of p53. Other proteins, such as Pin 1, Parc, and p300, and p300/CBP-associated factor (PCAF) histone acetyltransferases regulate the transactivation activity of p53. For efficient repair, especially in non-dividing cells, cellular levels of deoxyribonucleotides are increased during the DNA damage repair by p53-dependent transcriptional induction of the ribonucleotide reductase RRM2B (p53R2). It is accepted that the severity of DNA damage is the critical factor in directing the signaling cascade toward reversible cell cycle arrest or apoptosis. As part of the signaling cascade, the abundance of p53 protein, specific posttranslational modifications, and its interaction with downstream effectors, such as GADD45a or p21, may be responsible for directing the cellular response at this decision point.

Other pathways besides DNA and p53 can be involved in the cellular response to exposure to ionizing radiation. For example, ionizing radiation can produce reactive oxygen species (ROS) in the cytoplasm.

Low-dose radiotherapy (LD-RT) is known to exert an anti-inflammatory effect. In vitro models have revealed anti-inflammatory effects of LD-RT in doses ranging from 0.1-1.0 Gy on immune cells such as macrophages and neutrophils. Studies have also shown that low-dose radiation therapy has an anti-inflammatory effect involving diminished CCL20 chemokine expression and granulocyte/endothelial cell adhesion. An in vitro study by Khaw et al. (1991, British Journal of Ophthalmology 75:580-583) of beta irradiation of fibroblasts in culture found that "radiation reduces the proliferation of human Tenon's capsule fibroblasts. The doses of radiation which inhibited cell proliferation more than 50% (at day 7 and 14) and yet did not cause a decrease in the cell population were 500, 750, and 1000 rads." The fibroblasts enter a period of growth arrest but do not die.

The present invention features brachytherapy (beta radiation) used in combination with MIGS implants as described herein, wherein the brachytherapy helps to prevent or reduce bleb scarring or failure to maintain a functioning bleb. Without wishing to limit the present invention to any theory or mechanism, it is believed that the brachytherapy herein (e.g., low to intermediate dose of radiation) can inhibit or reduce inflammation and/or fibrogenesis by downregulating cellular (e.g., fibroblast) activity without cell death.

The application of beta radiation provides a medicament-like treatment, similar to a drug, wherein the beta radiation, when consumed by the cells, causes biological changes in signaling and gene transcription, thereby affecting cellular activity and growth, e.g., cell cycle arrest.

The present invention provides compositions or products that are radioactive compositions (sources of beta radiation). The radioactive composition has a therapeutic effect via the generation of beta radiation by, for example, the mechanisms previously discussed. In generating the beta radiation, radioactive composition is consumed (e.g., the product is gradually used up), in that the radioisotope atoms of the beta radioisotope brachytherapy source decay into other nuclides.

Brachytherapy System

As previously discussed, the present invention provides a brachytherapy system for applying beta radiation to a target of the eye, the target being a site of a bleb in an eye being treated for glaucoma with a MIGS implant or MIGS procedure. The brachytherapy system comprises a radionuclide brachytherapy source (RBS) for supplying the beta radiation that is delivered to the target.

The RBS of the present invention is constructed in a manner that is consistent with the Federal Code of Regulations, but is not limited to the terms mentioned in the Code. For example, the RBS of the present invention may further comprise a substrate. Also, for example, in addition to being enclosed by the mentioned "gold, titanium, stainless steel, or platinum", in some embodiments the radionuclide (isotope) of the present invention may be enclosed by a combination of one or more of "gold, titanium, stainless steel, or platinum". In some embodiments, the radionuclide (isotope) of the present invention may be enclosed by one or more layers of an inert material comprising silver, gold, titanium, stainless steel, platinum, tin, zinc, nickel, copper, other metals, ceramics, glass, or a combination of these.

In some embodiments, the RBS comprises a substrate, a radioactive isotope (e.g., Sr-90, Y-90, Rh-106, P-32, etc.), and an encapsulation. In some embodiments, the isotope is coated on the substrate, and both the substrate and isotope are further coated with the encapsulation. In some embodiments, the radioactive isotope is embedded in the substrate. In some embodiments, the radioactive isotope is part of the substrate matrix. In some embodiments, the encapsulation may be coated onto the isotope, and optionally, a portion of the substrate. In some embodiments, the encapsulation is coated around the entire substrate and the isotope. In some embodiments, the encapsulation encloses the isotope. In some embodiments, the encapsulation encloses the entire substrate and the isotope. In some embodiments, the radioactive isotope is an independent piece and is sandwiched between the encapsulation and the substrate.

In some embodiments, a surface on the substrate is shaped in a manner to provide a controlled projection of radiation. The substrate may be constructed from a variety of materials. For example, in some embodiments the substrate is constructed from a material comprising, a silver, an aluminum, a stainless steel, tungsten, nickel, tin, zirconium, zinc, copper, a metallic material, a ceramic material, a ceramic matrix, the like, or a combination thereof. In some embodiments, the substrate functions to shield a portion of the radiation emitted from the isotope. The encapsulation may be constructed from a variety of materials, for example from one or more layers of an inert material comprising a steel, a silver, a gold, a titanium, a platinum, another bio-compatible material, the like, or a combination thereof.

The radionuclide brachytherapy source (RBS) is constructed to provide a substantially uniform radiation dose across the target. For example, FIG. 12 shows how previous radiation applicators may only treat the center part of the target or under-dose the peripheral area and/or overdose the center. The present invention may provide a more uniform dose across the target area, e.g., as shown in FIG. 13 (most of the target area, e.g., an area within 3-4 mm away from the center, gets a dose that is at least 80-90% of the dose at the center and the center is not overdosed). However, the present invention is not limited to the dosimetry profile shown in FIG. 13.

In some embodiments, the target area is the entire bleb, e.g., the perimeter of the bleb, the center of the bleb, and the portions of the bleb in between the perimeter and the center. In some embodiments, the target area is the perimeter of the bleb, e.g., a ring-shaped target area. In some embodiments, the target is the perimeter of the bleb and a portion of the bleb next to the perimeter, e.g., the target may be annulus-shaped. In some embodiments, the target is a portion of the bleb in between the center and the perimeter. In some embodiments, the target is at least a portion of the center of the bleb. The present invention is not limited to the aforementioned descriptions of target areas.

In some embodiments, the RBS is designed such that the dose received at the perimeter of the bleb is higher than that received at the center of the bleb.

In some embodiments, the RBS is designed such that the dose received at the perimeter of the bleb is similar to that at the center, e.g., not less than 80% of the dose of the center, not less than 90% of the dose at the center, etc. In some embodiments, the RBS is designed such that any point of the target is within 20% of the dose of any other point of the target, e.g., the variation of dose across the target is not more than 20%, e.g., at any given point the variation is not more than 20%. In some embodiments, the RBS is designed such that any point of the target is within 15% of the dose of any other point of the target, e.g., the variation of dose across the target is not more than 15%, e.g., at any given point the variation is not more than 15%. In some embodiments, the RBS is designed such that any point of the target is within 10% of the dose of any other point of the target, e.g., the variation of dose across the target is not more than 10%, e.g., at any given point the variation is not more than 10%. In some embodiments, the RBS is designed such that any point of the target is within 8% of the dose of any other point of the target, e.g., the variation of dose across the target is not more than 8%, e.g., at any given point the variation is not more than 8%. In some embodiments, the RBS is designed such that any point of the target is within 5% of the dose of any other point of the target, e.g., the variation of dose across the target is not more than 5%, e.g., at any given point the variation is not more than 5%. In some embodiments, the RBS is designed such that any point of the target is within 3% of the dose of any other point of the target, e.g., the variation of dose across the target is not more than 3%, e.g., at any given point the variation is not more than 3%.

With respect to the aforementioned dose profiles, because the target area, and Planning Treatment Volume, has a small depth (e.g., 0.3 mm), the doses cited refer to the doses adjacent to the surface of the device, for example at a depth of 0.15 mm. In other embodiments, the doses cited may refer to the doses at a depth of 0.05, 0.1, 0.2, 0.25, 0.3, 0.35, 0.4, 0.45, or 0.5 mm.

Iterative computer simulations of output dosimetry may be used to determine an optimized design of device. Film dosimetry is a method of measuring radioactive delivery from a source and can be used to measure the dose across the target. It can also be used to calibrate or compare radioactive sources or to determine the homogeneity of the dose pattern.

The RBS may be disc shaped or have an annulus or rounded shape; however, the present invention is not limited to those shapes, and any shape that achieves a desired dose profile is encompassed herein. The shape of the RBS may help provide a controlled projection of radiation (e.g., a therapeutic dose) onto the target. The shape of the RBS may help the radiation dose to fall off quickly at the periphery of the target (whatever the target is determined to be, e.g., the whole bleb, a portion of the bleb, etc.). This may help keep the radiation within a limited area/volume and may help prevent unwanted exposure of structures such as the lens to radiation.

In some embodiments, the RBS has a diameter from 4 to 20 mm. In some embodiments, the RBS has a diameter from 5 to 15 mm. In some embodiments, the RBS has a diameter from 10 to 20 mm. In some embodiments, the RBS has a diameter from 10 to 15 m. In some embodiments, the RBS has a diameter from 5 to 7 mm (e.g., 5 mm, 6 mm, 7 mm). In some embodiments, the RBS has a diameter from 7 to 10 mm (e.g., 7 mm, 7.5 mm, 8 mm, 8.5 mm, 9 mm, 9.5 mm, 10 mm). In some embodiments, the RBS has a diameter from 9 to 12 mm (e.g., 9 mm, 9.5 mm, 10 mm, 10.5 mm, 11 mm, 11.5 mm, 12 mm). In some embodiments, the RBS has a diameter from 10 to 14 mm (e.g., 10 mm, 10.5 mm, 11 mm, 11.5 mm, 12 mm, 12.5 mm, 13 mm, 13.5 mm, 14 mm). In some embodiments, the RBS has a diameter from 12 to 16 mm (e.g., 12 mm, 12.5 mm, 13 mm, 13.5 mm, 14 mm, 14.5 mm, 15 mm, 15.5 mm, 16 mm). In some embodiments, the RBS has a diameter from 14 to 18 mm (e.g., 14 mm, 14.5 mm, 15 mm, 15.5 mm, 16 mm, 16.5 mm, 17 mm, 17.5 mm, 18 mm). In some embodiments, the RBS has a diameter of 3 mm. In some embodiments, the RBS has a diameter of 4 mm. In some embodiments, the RBS has a diameter of 5 mm. In some embodiments, the RBS has a diameter of 6 mm. In some embodiments, the RBS has a diameter of 7 mm. In some embodiments, the RBS has a diameter of 8 mm. In some embodiments, the RBS has a diameter of 9 mm. In some embodiments, the RBS has a diameter of 10 mm. In some embodiments, the RBS has a diameter of 11 mm. In some embodiments, the RBS has a diameter of 12 mm. In some embodiments, the RBS has a diameter of 13 mm. In some embodiments, the RBS has a diameter of 14 mm. In some embodiments, the RBS has a diameter of 15 mm. In some embodiments, the RBS has a diameter of 16 mm. In some embodiments, the RBS has a diameter of 17 mm. In some embodiments, the RBS has a diameter of 18 mm. In some embodiments, the RBS has a diameter of 19 mm. In some embodiments, the RBS has a diameter of 20 mm. In some embodiments, the RBS has a diameter more than 20 mm.

In some embodiments, the RBS delivers a radiation dose of 1000 cGy (10Gy) to the target. In some embodiments, the RBS delivers a radiation dose of 900 cGy to the target. In some embodiments, the RBS delivers a radiation dose of 800 cGy to the target. In some embodiments, the RBS delivers a radiation dose of 750 cGy to the target. In some embodiments, the RBS delivers a radiation dose of 600 cGy to the target. In some embodiments, the RBS delivers a radiation dose of 500 cGy to the target. In some embodiments, the RBS delivers a radiation dose of 400 cGy to the target. In some embodiments, the RBS delivers a radiation dose of 300 cGy to the target. In some embodiments, the RBS delivers a radiation dose of 200 cGy to the target. In some embodiments, the RBS delivers a radiation dose of 100 cGy to the target. In some embodiments, the RBS delivers a radiation dose of 50 cGy to the target. In some embodiments, the RBS delivers a radiation dose of 1100 cGy to the target. In some embodiments, the RBS delivers a radiation dose of 1200 cGy to the target. In some embodiments, the RBS delivers a radiation dose of 1300 cGy to the target. In some embodiments, the RBS delivers a radiation dose of 1500 cGy to the target. In some embodiments, the RBS delivers a radiation dose from 600 cGy and 1500 cGy to the target. In some embodiments, the RBS delivers a radiation dose from 50 cGy to 100 cGy. In some embodiments, the RBS delivers a radiation dose from 100 cGy to 150 cGy. In some embodiments, the RBS delivers a radiation dose from 150 cGy to 200 cGy. In some embodiments, the RBS delivers a radiation dose from 200 cGy to 250 cGy. In some embodiments, the RBS delivers a radiation dose from 250 cGy to 300 cGy. In some embodiments, the RBS delivers a radiation dose from 300 cGy to 350 cGy. In some embodiments, the RBS delivers a radiation dose from 350 cGy to 400 cGy. In some embodiments, the RBS delivers a radiation dose from 400 cGy to 450 cGy. In some embodiments, the RBS delivers a radiation dose from 450 cGy to 500 cGy. In some embodiments, the RBS delivers a radiation dose from 500 cGy to 550 cGy. In some embodiments, the RBS delivers a radiation dose from 550 cGy to 600 cGy. In some embodiments, the RBS delivers a radiation dose from 600 cGy to 650 cGy. In some embodiments, the RBS delivers a radiation dose from 650 cGy to 700 cGy. In some embodiments, the RBS delivers a radiation dose from 700 cGy to 750 cGy. In some embodiments, the RBS delivers a radiation dose from 750 cGy to 800 cGy. In some embodiments, the RBS delivers a radiation dose from 800 cGy to 850 cGy. In some embodiments, the RBS delivers a radiation dose from 850 cGy to 900 cGy. In some embodiments, the RBS delivers a radiation dose from 900 cGy to 950 cGy. In some embodiments, the RBS delivers a radiation dose from 950 cGy to 1000 cGy. In some embodiments, the RBS delivers a radiation dose from 1000 cGy to 1050 cGy. In some embodiments, the RBS delivers a radiation dose from 1050 cGy to 1100 cGy. In some embodiments, the RBS delivers a radiation dose from 1100 cGy to 1150 cGy. In some embodiments, the RBS delivers a radiation dose from 1150 cGy to 1200 cGy. In some embodiments, the RBS delivers a radiation dose from 1200 cGy to 1250 cGy. In some embodiments, the RBS delivers a radiation dose from 1250 cGy to 1300 cGy. In some embodiments, the RBS delivers a radiation dose from 1300 cGy to 1350 cGy. In some embodiments, the RBS delivers a radiation dose from 1350 cGy to 1400 cGy. In some embodiments, the RBS delivers a radiation dose from 1400 cGy to 1450 cGy. In some embodiments, the RBS delivers a radiation dose from 1450 cGy to 1500 cGy. In some embodiments, the RBS delivers a radiation dose from 1500 cGy to 1550 cGy. In some embodiments, the RBS delivers a radiation dose from 1550 cGy to 1600 cGy. In some embodiments, the RBS delivers a radiation dose from 1600 cGy to 1800 cGy. In some embodiments, the RBS delivers a radiation dose from 1800 cGy to 2000 cGy. In some embodiments, the RBS delivers a radiation dose of 600, 650, 700, 750, 800, 850, 900, 950, 1000, 1050, 1100, 1150, 1200, 1250, 1300, 1350, 1400, 1450, or 1500 cGy to the target. In some embodiments, the RBS delivers a radiation dose of 1500 to 3200 cGy. In some embodiments, the RBS delivers a radiation dose of 3200 to 8000 cGy. In some embodiments, the RBS delivers a radiation dose of 8000 cGy to 10000 cGy. In some embodiments, the RBS delivers a radiation dose of greater than 10000 cGy.

In some embodiments, the RBS delivers the prescribed dose in a time from 10 seconds to 20 minutes. In some embodiments, the RBS delivers the prescribed dose in a time from 20 seconds and 10 minutes. In some embodiments, the RBS delivers the prescribed dose in a time from 20 seconds to 60 seconds. In some embodiments, the RBS delivers the prescribed dose in a time from 30 seconds to 90 seconds. In some embodiments, the RBS delivers the prescribed dose in a time from 60 seconds to 90 seconds. In some embodiments, the RBS delivers the prescribed dose in a time from 90 seconds to 2 minutes. In some embodiments, the RBS delivers the prescribed dose in a time from 2 minutes to 3 minutes.

In some embodiments, the RBS delivers the prescribed dose in a time from 3 minutes to 4 minutes. In some embodiments, the RBS delivers the prescribed dose in a time from 3 minutes to 5 minutes. In some embodiments, the RBS delivers the prescribed dose in a time from 3 minutes to 6 minutes. In some embodiments, the RBS delivers the prescribed dose in a time from 4 minutes to 5 minutes. In some embodiments, the RBS delivers the prescribed dose in a time from 4 minutes to 6 minutes. In some embodiments, the RBS delivers the prescribed dose in a time from 5 minutes to 6 minutes. In some embodiments, the RBS delivers the prescribed dose in a time from 6 minutes to 7 minutes. In some embodiments, the RBS delivers the prescribed dose in a time from 7 minutes to 8 minutes. In some embodiments, the RBS delivers the prescribed dose in a time from 8 minutes to 9 minutes. In some embodiments, the RBS delivers the prescribed dose in a time from 9 minutes to 10 minutes. In some embodiments, the RBS delivers the prescribed dose in a time from 10 minutes to 12 minutes. In some embodiments, the RBS delivers the prescribed dose in a time from 12 minutes to 15 minutes. In some embodiments, the RBS delivers the prescribed dose in a time from 15 minutes to 20 minutes.

In some embodiments, the RBS delivers the prescribed dose in 25 seconds. In some embodiments, the RBS delivers the prescribed dose in 45 seconds. In some embodiments, the RBS delivers the prescribed dose in 60 seconds. In some embodiments, the RBS delivers the prescribed dose in 90 seconds. In some embodiments, the RBS delivers the prescribed dose in 2 minutes. In some embodiments, the RBS delivers the prescribed dose in 3 minutes. In some embodiments, the RBS delivers the prescribed dose in 4 minutes. In some embodiments, the RBS delivers the prescribed dose in 5 minutes. In some embodiments, the RBS delivers the prescribed dose in 6 minutes. In some embodiments, the RBS delivers the prescribed dose in 7 minutes. In some embodiments, the RBS delivers the prescribed dose in 8 minutes. In some embodiments, the RBS delivers the prescribed dose in 9 minutes. In some embodiments, the RBS delivers the prescribed dose in 10 minutes. In some embodiments, the RBS delivers the prescribed dose in 11 minutes. In some embodiments, the RBS delivers the prescribed dose in 12 minutes. In some embodiments, the RBS delivers the prescribed dose in 13 minutes. In some embodiments, the RBS delivers the prescribed dose in 14 minutes. In some embodiments, the RBS delivers the prescribed dose in 15 minutes. In some embodiments, the RBS delivers the prescribed dose in 16 minutes. In some embodiments, the RBS delivers the prescribed dose in 17 minutes. In some embodiments, the RBS delivers the prescribed dose in 18 minutes. In some embodiments, the RBS delivers the prescribed dose in 19 minutes. In some embodiments, the RBS delivers the prescribed dose in 20 minutes. In some embodiments, the RBS delivers the prescribed dose in a time frame greater than 20 minutes.

In some embodiments, a dose (e.g., a prescribed dose) may be delivered in a single application. In other embodiments, a dose (e.g., a prescribed dose) may be fractionated and applied in multiple applications. For example, in some embodiments, radiation (e.g., a prescribed dose) may be applied over the course of 2 applications. In some embodiments, radiation (e.g., a prescribed dose) may be applied over the course of 3 applications. In some embodiments, radiation (e.g., a prescribed dose) may be applied over the course of 4 applications. In some embodiments, radiation (e.g., a prescribed dose) may be applied over the course of 5 applications. In some embodiments, radiation (e.g., a prescribed dose) may be applied over the course of more than 5 applications. In some embodiments, radiation (e.g., a prescribed dose) may be applied over the course of 20 applications. In some embodiments, radiation (e.g., a prescribed dose) may be applied over the course of more than 20 applications.

Each application may deliver an equal sub-dose. In some embodiments, one or more of the sub-doses are different. For example, one or more of the sub-doses may be different so as to increase or decrease with each additional application.

According to one embodiment, a dose of radiation may be applied prior to the procedure for implantation of a MIGS device. For example, in some embodiments, a dose of radiation may be applied one or more days prior to the MIGS implantation surgery (e.g., insertion of the MIGS device). In some embodiments, a dose of radiation may be applied within a 24-hour prior before the MIGS implantation surgery (e.g., insertion of the MIGS device). In some embodiments, a dose of radiation may be applied just prior to the MIGS implantation surgery (e.g., insertion of the MIGS device), e.g., 1 hour before, 30 minutes before, 15 minutes before, 5 minutes before 1 minute before, etc. In some embodiments, a dose of radiation may be applied during the procedure for implantation of a MIGS device. In some embodiments, a dose of radiation may be applied right after the MIGS device is implanted, e.g., within 1 minute, 2 minutes, 3 minutes, 5 minutes, 10 minutes, etc.). In some embodiments, a dose of radiation may be applied before an incision is made into the conjunctiva. In some embodiments, a dose of radiation may be applied after an incision is made into the conjunctiva. In other embodiments, a dose of radiation may be applied after the MIGS implantation surgery (e.g., insertion of the MIGS device). In some embodiments, a dose of radiation may be applied within a 24-hour period after the MIGS implantation surgery (e.g., insertion of the MIGS device). In some embodiments, a dose of radiation may be applied within one to two days after the MIGS implantation surgery (e.g., insertion of the MIGS device). In some embodiments, a dose of radiation may be applied within 2 or more days after the MIGS implantation surgery (e.g., insertion of the MIGS device). In some embodiments the dose may be applied any time after the glaucoma surgery. In some embodiments, the dose is applied months or years after the glaucoma surgery. For example, a dose may be given to patients that did not receive a dose during surgery but at a future date have scar or needling procedures to break up scar tissue.

Brachytherapy Applicator

The present invention also provides applicators for applying the beta radiation to the target in the eye. In certain embodiments, the applicator may feature the RBS fixedly attached to the applicator. In some embodiments, the RBS is loaded in the applicator prior to its use in surgery. Devices may be similar to these originally used for pterygium or other ophthalmic applications. For example, the Technical Information and Instruction Manual for Users of the Beta Therapy Source Model 67-850, Nuclear Associates Manual lists multiple ophthalmic brachytherapy indications for use including: tumors, hemangioma, pterygium, vascularization, and irritable scar. However, the present invention is not limited to these previously made devices.

The applicator may be constructed from any appropriate material, such as a biocompatible material or a combination of materials. Non-limiting examples of biocompatible materials include, but are not limited to, metals (for example, stainless steel, titanium, gold), ceramics and polymers.

The applicator may comprise a handle adapted to hold the RBS, e.g., the RBS may be positioned at a distal end of the handle. In some embodiments, the applicator of the present invention comprises a radiation attenuation mask for shaping the radiation in a particular manner. For example, the mask may limit the amount of radiation that reaches non-target tissues such as the lens.

In some embodiments, the applicator features a removable cap for temporarily shielding the RBS or for keeping the applicator or RBS sterile.

In some embodiments, one or more components of the invention (e.g., applicator) are constructed from a material that can further shield the user from the RBS. In some embodiments, a material having a low atomic number (Z) may be used for shielding (e.g., polymethyl methacrylate). In some embodiments, one or more layers of material are used for shielding, wherein an inner layer comprises a material having a low atomic number (e.g., polymethyl methacrylate) and an outer layer comprises lead.

As an example, in some embodiments, the present invention is a device loaded from a Ruthenium-106 cow with an activity of rhodium-106 providing for the prescribed dose. The device can be applied to the target volume to deliver the full activity of its contents. For example, the device may be placed over the target lesion for 10 half-lives (300 seconds), delivering all its radioactive energy and consuming the rhodium-106, depleting it to palladium.

As an example, in some embodiments, the present invention is an applicator constructed containing Strontium-90/Yttrium-90 radioisotopes in secular equilibrium. In some embodiments, the Sr-90/Y-90 is in a sealed source brachytherapy device, e.g., constructed of stainless steel. The source may be constructed to project a dose of about 1,000 cGy per unit time into a sufficient portion of the adjacent Planning Treatment Volume, e.g., to contain the conjunctival tissue to a depth of 0.3 mm. The source may be secured to a handle, and a radiation attenuation mask (shaped as a fan) is fixed to the source. The source may be covered with a sterile barrier. The present invention is not limited to this embodiment, and variations and combinations of the disclosed features are also covered in the scope of this application.

Methods

As previously discussed, the present invention provides methods for applying beta radiation to a target of the eye, for example the site of a bleb formed by a MIGS implant or procedure. Without wishing to limit the present invention to any theory or mechanism, it is believed that the use of beta radiation to treat the site of the bleb is advantageous because the application of beta radiation can be rapid and simple, and the effects can be long lasting. Further, beta radiation may be advantageous since it does not require post-operative compliance.

In some embodiments, the methods herein inhibit or reduce fibrogenesis in a bleb associated with a MIGS implant or procedure. In some embodiments, the methods herein inhibit or reduce inflammation in a bleb associated with a MIGS implant or procedure.

In some embodiments, the methods herein maintain the function of a bleb associated with a MIGS implant or procedure. In some embodiments, the methods herein enhance the function of a MIGS implant, e.g., by maintaining a functional bleb. In some embodiments, the methods herein reduce intraocular pressure (IOP), maintain a healthy IOP, treat glaucoma, etc.

The methods herein may comprise implanting a Minimally Invasive Glaucoma Surgery (MIGS) implant within the eye. MIGS implants are discussed in detail above. Generally, the MIGS implant is inserted trans-sclerally and causes formation of a bleb in the subconjunctival space of the eye or in a space between the conjunctiva and Tenon's capsule. For example, the MIGS implant may be placed between the anterior chamber of the eye and a subconjunctival space. In some embodiments, the MIGS implant is placed between the anterior chamber of the eye and a space between the conjunctiva and Tenon's capsule.

The methods herein comprise applying beta radiation to a target area of the eye. In some embodiments, the target area is a site of the bleb or an expected site of the bleb. In some embodiments, the target area surrounds the end of the implant. In some embodiments, the target is from 2 to 5 mm in diameter. In some embodiments, the target is from 5 to 12 mm in diameter. In some embodiments, the target is from 0.3 mm to 0.5 mm in thickness.

In some embodiments, the beta radiation is applied prior to the insertion of the MIGS implant. In some embodiments, the beta radiation is applied after the insertion of the MIGS implant.

In some embodiments, the methods herein further comprise introducing a drug to a site, e.g., a site of the MIGS implant, a site of the bleb, a different part of the eye.

As previously discussed, ionizing radiation has effects on cells that can lead to cell cycle arrest. In some embodiments, the beta radiation of the present invention causes cell cycle arrest in fibroblasts on or associated with the Tenon's capsule or conjunctiva so as to inhibit or reduce the fibrotic process and inflammation that leads to bleb failure.

As previously discussed, the beta radiation may be applied via a radionuclide brachytherapy source (RBS). The RBS may be applied to the target via an applicator. As previously discussed, in some embodiments, the beta radiation is Strontium-90 (Sr-90), Phosphorus-32 (P-32), Ruthenium 106 (Ru-106), Yttrium 90 (Y-90), or a combination thereof. As previously discussed, in some embodiments, the RBS provides a dose of about 750 cGy to the target. In some embodiments, the RBS provides a dose from 500 to 1000 cGy to the target.

The present invention also features methods for preparing an applicator for emitting beta radiation. In some embodiments, the method comprises inserting a radionuclide brachytherapy source (RBS) into a RBS cavity in an applicator. In some embodiments, the method comprises attaching the RBS to an applicator. In some embodiments, the applicator comprises a handle and a distal portion, wherein the distal portion is where the RBS is attached or is the site of the RBS cavity. In some embodiments, the RBS is constructed to emit a radiation dose at 4 mm from its center that is at least 90% of that emitted at the center. The present invention is not limited to an RBS emitting a radiation dose at 4 mm from its center that is at least 90% of that emitted at the center. Alternative examples of dose distributions are described herein.

Additional Applications

Needling procedures to the bleb are generally preformed to free or remove scar tissue and/or cystic structures about the bleb and surgery site that may later arise from wound healing or scarring or inflammatory responses to the glaucoma surgery. Needling procedures may affect surgical site morphology, restore the function of the surgery and/or lower the IOP.

An example of a surgical procedure for bleb revision with needling includes the following steps: After instillation of topical anesthetic and antibiotic drops, a cotton tip applicator soaked in topical anesthetic is applied for 2 minutes to the conjunctival site where the needle will enter. A lid speculum is placed in the eye. At the slit lamp, the patient is instructed to look down so all of the bleb is exposed. The slit lamp is set at the lowest magnification. This facilitates visualization of the bleb even if the patient moves his eye during the procedure. Needling is performed with a 27-gauge needle on a tuberculin syringe. The needle is introduced into the subconjunctival space, 1 mm from the edge of the bleb, and advanced into the bleb. The subconjunctival fibrosis is cut with a firm back-and-forth motion. The needle is then advanced in the same plane into the other side of the scleral flap, and the fibrous tissue is cut. The needle is then partially withdrawn from the bleb and the direction changed to parallel the edge of the bleb; with sweeping motions, the scar tissue is cut. The goal is to cut the fibrous tissue in all directions around the scleral flap. The needle is then withdrawn. An antimetabolite may be injected into the bleb concomitant with the needling procedure.

The methods and compositions of the present invention may be used in combination with needling procedures. For example, the methods herein may feature applying beta radiation from a radioisotope to a bleb (e.g., a bleb from a glaucoma device or procedure such as a MIGS device, trabeculectomy, etc.) that is about to undergo needling, e.g., from 3 to 6 weeks before, from 1 to 3 weeks before, from 3 to 7 days before, from 24 to 72 hours before, from 12 to 24 hours before, from 6 to 12 hours before, from 3 to 6 hours before, from 2 to 3 hours before, from 1 to 2 hours before, from 30 to 60 minutes before, from 20 to 30 minutes before, from 10 to 20 minutes before, from 1 to 10 minutes before, etc. In some embodiments, the methods feature applying the beta radiation to a bleb (e.g., a bleb from a glaucoma device or procedure such as a MIGS device, trabeculectomy, etc.) that has previously undergone needling, e.g., from 0.5 to 10 minutes after, from 10 to 20 minutes after, from 20 to 30 minutes after, from 30 to 60 minutes after, from 1 to 2 hours after, from 2 to 3 hours after, from 3 to 6 hours after, from 6 to 12 hours after, from 12 to 24 hours after, from 24 to 72 hours after, from 3 to 7 days after, from 1-3 weeks after, from 3 to 6 weeks after, etc.

Without wishing to limit the present invention to any theory or mechanism, it is believed that treating scar tissue formation on a bleb formed by a trabeculectomy procedure is different than treating a newly-created (and scar tissue-free) bleb at the time of the trabeculectomy. In some embodiments, the methods herein further comprise applying beta therapy concomitant with a needling procedure to a bleb formed by a trabeculectomy procedure. In some embodiments, the methods herein further comprise applying beta therapy to a trabeculectomy bleb that has formed scar tissue. In some embodiments, the methods herein further comprise applying beta therapy to a bleb in the eye of a trabeculectomy patient where the intraocular pressure (IOP) has increased. In some embodiments, the methods herein further comprise applying beta therapy to a bleb where the trabeculectomy is failing or has failed. In some embodiments, the methods herein further comprise applying beta therapy to a bleb in a second trabeculectomy, where the first trabeculectomy has failed.

In some embodiments, the methods herein further comprise applying beta therapy to a bleb that is failing or has failed. In some embodiments, the methods herein further comprise applying beta therapy to a MIGS device bleb that is failing or has failed. In some embodiments, the methods herein further comprise applying beta therapy to a MIGS device bleb that has formed scar tissue. In some embodiments, the methods herein further comprise applying beta therapy to a bleb in the eye of a MIGS device patient where the intraocular pressure (IOP) has increased.

In some embodiments, the methods herein further comprise applying another drug in addition to beta radiation. In some embodiments, the methods herein further comprise applying another antimetabolite (e.g., mitomycin-c or 5-fluorouracil) in addition to beta radiation.

The methods, systems, and compositions of the present invention may also be applied to wound healing, e.g., wounds in the eye due to foreign body insertion, trauma, ocular surface wounds, etc. One model of wound healing divides the process into hemostasis, inflammation, proliferation, and remodeling. The first phase of hemostasis begins immediately after wounding, with vascular constriction and fibrin clot formation. The clot and surrounding wound tissue release pro-inflammatory cytokines and growth factors such as transforming growth factor (TGF)-β, platelet-derived growth factor (PDGF), fibroblast growth factor (FGF), and epidermal growth factor (EGF). Once bleeding is controlled, inflammatory cells migrate into the wound and promote the inflammatory phase, which is characterized by the sequential infiltration of neutrophils, macrophages, and lymphocytes. In the early wound, macrophages release cytokines that promote the inflammatory response by recruiting and activating additional leukocytes. As macrophages clear these apoptotic cells, they undergo a phenotypic transition to a reparative state that stimulates keratinocytes, fibroblasts, and angiogenesis to promote tissue regeneration. T-lymphocytes migrate into wounds following the inflammatory cells and macrophages, and peak during the late-proliferative/early-remodeling phase. T-cells regulate many aspects of wound healing, including maintaining tissue integrity, defending against pathogens, and regulating inflammation. The proliferative phase generally follows and overlaps with the inflammatory phase, and is characterized by epithelial proliferation and migration over the provisional matrix within the wound (re-epithelialization). In the reparative dermis, fibroblasts and endothelial cells are the most prominent cell types present and support capillary growth, collagen formation, and the formation of granulation tissue at the site of injury. Within the wound bed, fibroblasts produce collagen as well as glycosaminoglycans and proteoglycans, which are major components of the extracellular matrix (ECM). Following robust proliferation and ECM synthesis, wound healing enters the final remodeling phase, which can last for years.

The present invention may feature applying beta radiation to ocular wounds, such as wounds due to the presence of a foreign body or trauma.

EXAMPLES

Example 1: Surgical Procedure for XEN® Implant (AqueSys, Inc.), an Example of a Flow-Controlled MIGS Device The present invention provides an example of a surgical procedure for implantation of a XEN® (AqueSys, Inc.) MIGS device, an example of a flow-controlled MIGS device. FIG. 9A, FIG. 9B, FIG. 9C, and FIG. 9D also show a schematic drawing of the process of implanting a XEN® implant (AqueSys, Inc.). The present invention is in no way limited to the specific steps, methods, devices, systems, and compositions described herein.

First, the surgical field is readied, and the patient is anesthetized. Surgeons may opt to use a regional block to minimize the potential for patient or ocular movements that may lead to iatrogenic trauma; alternatively, the use of topical anesthesia alone may be sufficient for surgical comfort.

The conjunctiva is marked with ink at the desired implant location. The target site may be 3 mm posterior to the cornea limbus. Additional marks either side of the target may also be made.

In some procedures, a small bleb is formed by injection under the conjunctiva of Balanced Saline Solution or air followed by ophthalmic viscoelastic.

The globe is stabilized with a probe placed against the sclera. A clear corneal incision is made using a 1.1 mm paracentesis blade. A Vera Hook is placed into the incision to stabilize the eye during the procedure by providing counter traction.

A 1.8 mm Keratome blade is used to enter the anterior chamber. The incision is made 180° from the intended stent location. The incision is angled toward the targeted quadrant of the stent placement.

The anterior chamber is stabilized with the addition of ophthalmic viscoelastic.

Following preparation of the injector, the tip is inserted through the primary incision and the needle is advanced through the anterior chamber. Visualization by gonioscopy may be used in guiding the injector to the target location in the angle. The injector needle tip is placed just anterior to the trabecular meshwork in the angle. The needle is advanced through the sclera with the entire bevel emerging into the subconjunctival space at the target site. The needle bevel is rotated and pressed up against the scleral wall.

Advancing the injector plunger both deploys the stent, and causes the distal end of the needle to retract out of the scleral tissue. The injector is then withdrawn from the anterior chamber.

Visualization by gonioscopy is then used to ensure that about 1.0 mm of the implant projects into the angle and that placement is immediately anterior to the pigmented trabecular meshwork. The bleb is then inspected. The conjunctiva is checked to ensure it is intact. Visualization ensures that 3 mm of distal end of the gel stent is lying flat and freely mobile in the subconjunctival space.

Viscoelastic is evacuated and thoroughly rinsed from the anterior chamber. If present, any blood is thoroughly removed from the anterior chamber. Following this step, constant irrigation of balanced salt solution into the anterior chamber is preformed to prime the implant and induce formation of the bleb.

The surgeon also thoroughly hydrates all incisions to ensure that pressure and a formed anterior chamber are maintained. The clear cornea incision may be closed with fluid hydration. For a leaking incision, a 10-0 nylon suture may also be placed.

At the conclusion of surgery, the conjunctival area surrounding the tube may be exposed to beta irradiation with a radioactive brachytherapy source (RBS)-containing delivery device. In some embodiments, the probe may be placed over the posterior end of the tube, e.g., stopping about 1 mm from the limbus.

Example 2: Surgical Procedure for InnFocus MicroShunt® Implant (InnFocus, Inc., Santen Pharmaceutical Co.), an Example of a Flow-Controlled Stent The present invention provides an example of a surgical procedure for implantation of an InnFocus MicroShunt® (InnFocus, Inc., Santen Pharmaceutical Co.) MIGS device, an example of a flow-controlled stent. The present invention is in no way limited to the specific steps, methods, devices, systems, and compositions described herein.

First, the surgical field is readied and the patient anesthetized, e.g., using local anesthesia.

A conjunctival perimetery incision is made at the superior limbus of approximately 5 or 6 mm in length (fornix based incision). Tenon's insertion is cut and disinserted at about 2 mm back from the limbus. A conjunctival flap is created by lifting Tenon's capsule and the conjunctiva and bluntly dissecting posteriorly (in some embodiments with Westcott scissors).

Cautery is applied via a 23 gauge pencil cautery tip to the limbus incision site and episcleral surface to limit bleeding, and the area irrigated. The sclera is cleared with a Tookes knife.

The target implant location is marked with sterile ink. The target site is 3 mm posterior to the anterior limbus.

A scleral tunnel of 2 mm length originating from the ink mark towards the limbus is created with a 1 mm micro knife with a 2 mm bevel. A 25-gauge needle, bent at the hub, is inserted into the tunnel and advanced to the scleral spur. On further advancing of the needle beyond the scleral spur, the needle is directed downwards so as to enter into the anterior chamber on the plane of the iris. The needle is advanced into the anterior chamber, and then it is withdrawn.

The stent is advanced in the tunnel in a bevel up position. The tip of the shunt is observed entering the anterior chamber. The fins of the shunt are then inserted within the scleral tunnel.

Using a thin-wall 23 gauge cannula, balanced saline solution (BSS) is injected into the shunt. Alternatively, a paracentesis can be made and BSS injected into the anterior chamber. Patency of the shunt is confirmed by observing flow at the tip in the anterior chamber.

The distal end of the shunt device is placed under the conjunctival and Tenon's capsule flap.

Tenon's capsule and the conjunctiva are closed separately in two sutured closures using 9-0 polyglactin 910 on a blunt spatula needle. The final closure incorporates a horizontal mattress suture to prevent leaking.

Visualization by gonioscopy is then used to ensure that the device is visible in the anterior chamber at the level of the spur just anterior to the iris.

At the conclusion of surgery the conjunctival area surrounding the stent may be exposed to beta irradiation with a radioactive brachytherapy source (RBS)-containing delivery device. In some embodiments, the RBS is placed over the back end of the tube and the anterior part of the tube, e.g., stopping about 1 mm from the limbus.

Example 3: Surgical Procedure for Beta Radiation Application

The present invention provides an example of a procedure for the application of beta radiation to the eye. The present invention is in no way limited to the specific steps, methods, devices, systems, and compositions described herein.

Preparation and Assembly

The device assembly procedure is done behind a plexiglass beta shield (for example, the Large Dual Angle Beta Radiation Shield, Universal Medical Inc.). The medical technician or medical physicist opens the Radioisotope Brachytherapy Source (RBS) storage container. The RBS is removed from its container using remote handling techniques (for example, long forceps). The RBS is placed on a clean field.

The Manual Brachytherapy Applicator (MBA) assembly is a single-use sterile-packed device. Its packaging is checked by examining for damage or breach of the sterile barrier. Finding none, the applicator package is opened, and the applicator assembly placed on a sterile field.

The applicator assembly consists of a handle and RBS cap. Using aseptic technique and remote handling techniques, the RBS is loaded into the applicator. The handle is attached, and the sterile cap is attached. Care is taken not to cross contaminate the exterior of the sterile applicator with the clean RBS.

The radiation output is confirmed consistent with standards of quality assurance in radiation therapy (for example see: Palmer, Antony L., Andrew Nisbet, and David Bradley. "Verification of high dose rate brachytherapy dose distributions with EBT3 Gafchromic film quality control techniques." Physics in medicine and biology 58.3 (2013): 497). In one method of quality assurance, the applicator is applied to radiographic film in sterile overwrap for a specified dwell time. The overwrap is removed. The medical physicist checks the area of application for evidence of film exposure.

The device is placed into a sterile plexiglass beta transport box (for example the IBI Beta-Gard Acrylic Storage Container—Large, Universal Medical Inc.) and the box placed on the operative Mayo stand.

Previously the decayed activity of the RBS has been calculated to determine the contemporary dose per unit time (for example, cGy/second). The decay calculation methodology is known to those skilled in medical physics and is also described in the NRC Information Notice 96-66: United States Nuclear Regulatory Commission, Office of Nuclear Material Safety and Safeguards, Washington D.C. 20555, Dec. 13, 1996. The dwell time for the total prescribed dose is then calculated. As an example, the prescription dose is 1,000 cGy to a center point of 0.19 mm depth from the conjunctival surface. As an example, the decayed activity of the RBS is 30 cGy/second at a water equivalent depth of 0.19 mm. In this example, the dwell time is calculated to be about 33 seconds, providing a 990 cGy dose.

Surgical Application

The beta therapy is applied following completion of a glaucoma surgery for placement of a MIGs device, for example as described elsewhere in this application. The conjunctiva is either intact, or may have been surgically closed (for example, with 9-0 horizontal mattress suture). The eyelids are retracted with an eyelid speculum (for example a Barraquer wire speculum). The eye is rotated to a downward gaze position by the use of a probe placed against the sclera providing traction (for example the distal end of a Vera Hook placed against the eye). This allows better visual and surgical access to the superior conjunctiva.

The ophthalmic surgeon removes the Manual Brachytherapy Applicator device from its shielded box. The distal end (active end) of the applicator is placed over the sclera in a position just superior to the limbus. The diameter of the applicator encompasses the bleb. The area of application also encompasses the majority of the distal end of the MIGS shunt or stent, thus also specifically treating the conjunctiva that directly overlays the shunt or stent. The Manual Brachytherapy Applicator is held in place for the specified dwell time. In some embodiments, the dwell time has been programmed into a count-down clock. Following the specified dwell time, the Manual Brachytherapy Applicator is removed from the operative field and returned to the shielded acrylic box.

At the conclusion of surgery, antibiotic ointment is applied to the eye and the eye patched.

Following the surgery, the Manual Brachytherapy Applicator is disassembled behind the acrylic beta shield. The Radioisotope Brachytherapy Source is returned to its storage container. The disposable portions of the device are discarded in a manner consistent with appropriate disposal of biological waste (for example "red bag" waste).

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A method of maintaining a functioning drainage bleb in an eye of a patient being treated for glaucoma, the method comprising:
   a. implanting a Minimally Invasive Glaucoma Surgery (MIGS) implant within the eye, wherein the implant is inserted trans-sclerally and forms a bleb in a subconjunctival space of the eye or in a space between a conjunctiva and Tenon's capsule, wherein the bleb functions to drain aqueous humor; and
   b. applying a radioisotope that emits beta radiation to a target area of the eye, wherein the target area is at least a portion of the bleb;
wherein the beta radiation reduces or inhibits a fibrotic process and inflammation that causes bleb failure, wherein the beta radiation is effective to maintain the drainage function of the bleb, and wherein the portion of the bleb that is the target area is a perimeter of the bleb.

2. A method of maintaining a functioning drainage bleb in an eye of a patient being treated for glaucoma, the method comprising:
   a. implanting a Minimally Invasive Glaucoma Surgery (MIGS) implant within the eye, wherein the implant is inserted trans-sclerally and forms a bleb in a subconjunctival space of the eye or in a space between a conjunctiva and Tenon's capsule, wherein the bleb functions to drain aqueous humor; and
   b. applying a radioisotope that emits beta radiation to a target area of the eye, wherein the target area is at least a portion of the bleb;
wherein the beta radiation reduces or inhibits a fibrotic process and inflammation that causes bleb failure, wherein the beta radiation is effective to maintain the drainage function of the bleb, and wherein the portion of the bleb that is the target area is a perimeter of the bleb and a portion of the bleb between a center of the bleb and the perimeter of the bleb.

3. A method of maintaining a functioning drainage bleb in an eye of a patient being treated for glaucoma, the method comprising:
   a. implanting a Minimally Invasive Glaucoma Surgery (MIGS) implant within the eye, wherein the implant is inserted trans-sclerally and forms a bleb in a subconjunctival space of the eye or in a space between a conjunctiva and Tenon's capsule, wherein the bleb functions to drain aqueous humor; and
   b. applying a radioisotope that emits beta radiation to a target area of the eye, wherein the target area is at least a portion of the bleb;
wherein the beta radiation reduces or inhibits a fibrotic process and inflammation that causes bleb failure, wherein the beta radiation is effective to maintain the drainage function of the bleb, and wherein the target area surrounds an end of the MIGS implant.

4. A method of maintaining a functioning drainage bleb in an eye of a patient being treated for glaucoma, the method comprising:
   a. implanting a Minimally Invasive Glaucoma Surgery (MIGS) implant within the eye, wherein the implant is inserted trans-sclerally and forms a bleb in a subconjunctival space of the eye or in a space between a conjunctiva and Tenon's capsule, wherein the bleb functions to drain aqueous humor; and
   b. applying a radioisotope that emits beta radiation to a target area of the eye, wherein the target area is at least a portion of the bleb;
wherein the beta radiation reduces or inhibits a fibrotic process and inflammation that causes bleb failure, wherein the beta radiation is effective to maintain the drainage function of the bleb, and wherein the target area is from 2 to 12 mm in diameter.

5. A method of reducing intraocular pressure (IOP) in an eye, said method comprising:
   a. implanting a Minimally Invasive Glaucoma Surgery (MIGS) implant within an eye of a patient being treated for glaucoma, wherein the implant is inserted between an anterior chamber of the eye and a subconjunctival space of the eye or between the anterior chamber of the eye and a space between a conjunctiva and Tenon's capsule, wherein the implant forms a bleb for draining aqueous humor; and
   b. applying beta radiation from a radioisotope that emits beta radiation to a target area of the eye, wherein the target area is at least a portion of the bleb;
wherein the beta radiation is effective for maintaining function of the bleb to drain aqueous humor thereby reducing Intraocular Pressure (IOP) of the eye, and wherein the portion of the bleb that is the target area is a perimeter of the bleb.

6. A method of reducing intraocular pressure (IOP) in an eye, said method comprising:
   a. implanting a Minimally Invasive Glaucoma Surgery (MIGS) implant within an eye of a patient being treated for glaucoma, wherein the implant is inserted between an anterior chamber of the eye and a subconjunctival space of the eye or between the anterior chamber of the eye and a space between a conjunctiva and Tenon's capsule, wherein the implant forms a bleb for draining aqueous humor; and
   b. applying beta radiation from a radioisotope that emits beta radiation to a target area of the eye, wherein the target area is at least a portion of the bleb;
wherein the beta radiation is effective for maintaining function of the bleb to drain aqueous humor thereby reducing Intraocular Pressure (IOP) of the eye, and wherein the portion of the bleb that is the target area is a perimeter of the bleb and a portion of the bleb between a center of the bleb and the perimeter of the bleb.

7. A method of reducing intraocular pressure (IOP) in an eye, said method comprising:
   a. implanting a Minimally Invasive Glaucoma Surgery (MIGS) implant within an eye of a patient being treated for glaucoma, wherein the implant is inserted between an anterior chamber of the eye and a subconjunctival space of the eye or between the anterior chamber of the eye and a space between a conjunctiva and Tenon's capsule, wherein the implant forms a bleb for draining aqueous humor; and
   b. applying beta radiation from a radioisotope that emits beta radiation to a target area of the eye, wherein the target area is at least a portion of the bleb;
wherein the beta radiation is effective for maintaining function of the bleb to drain aqueous humor thereby reducing Intraocular Pressure (IOP) of the eye, and wherein the target area surrounds an end of the MIGS implant.

8. A method of reducing intraocular pressure (IOP) in an eye, said method comprising:
   a. implanting a Minimally Invasive Glaucoma Surgery (MIGS) implant within an eye of a patient being treated for glaucoma, wherein the implant is inserted between an anterior chamber of the eye and a subconjunctival space of the eye or between the anterior chamber of the eye and a space between a conjunctiva and Tenon's capsule, wherein the implant forms a bleb for draining aqueous humor; and
   b. applying beta radiation from a radioisotope that emits beta radiation to a target area of the eye, wherein the target area is at least a portion of the bleb;
wherein the beta radiation is effective for maintaining function of the bleb to drain aqueous humor thereby reducing Intraocular Pressure (IOP) of the eye, and wherein the target area is from 2 to 12 mm in diameter.

9. A method of reducing inflammation in an eye having a foreign body therein, the foreign body being a Minimally Invasive Glaucoma Surgery (MIGS) implant inserted between an anterior chamber of the eye and a subconjunctival space of the eye or between the anterior chamber of the eye and a space between a conjunctiva and Tenon's capsule, wherein the implant forms a bleb for draining aqueous humor, said method comprising: applying beta radiation from a radioisotope that emits beta radiation to a target area of the eye, and wherein the target area is at least a portion of the bleb; wherein the beta radiation is effective for reducing inflammation caused by the foreign body, and wherein the portion of the bleb that is the target area is a perimeter of the bleb.

10. A method of reducing inflammation in an eye having a foreign body therein, the foreign body being a Minimally Invasive Glaucoma Surgery (MIGS) implant inserted between an anterior chamber of the eye and a subconjunctival space of the eye or between the anterior chamber of the eye and a space between a conjunctiva and Tenon's capsule, wherein the implant forms a bleb for draining aqueous humor, said method comprising: applying beta radiation from a radioisotope that emits beta radiation to a target area of the eye, and wherein the target area is at least a portion of the bleb; wherein the beta radiation is effective for reducing inflammation caused by the foreign body, and wherein the portion of the bleb that is the target area is a perimeter of the bleb and a portion of the bleb between a center of the bleb and the perimeter of the bleb.

11. A method of reducing inflammation in an eye having a foreign body therein, the foreign body being a Minimally Invasive Glaucoma Surgery (MIGS) implant inserted between an anterior chamber of the eye and a subconjunctival space of the eye or between the anterior chamber of the eye and a space between a conjunctiva and Tenon's capsule, wherein the implant forms a bleb for draining aqueous humor, said method comprising: applying beta radiation from a radioisotope that emits beta radiation to a target area of the eye, and wherein the target area is at least a portion of the bleb: wherein the beta radiation is effective for reducing inflammation caused by the foreign body, and wherein the target area surrounds an end of the MIGS implant.

12. A method of reducing inflammation in an eye having a foreign body therein, the foreign body being a Minimally Invasive Glaucoma Surgery (MIGS) implant inserted between an anterior chamber of the eye and a subconjunctival space of the eye or between the anterior chamber of the eye and a space between a conjunctiva and Tenon's capsule, wherein the implant forms a bleb for draining aqueous humor, said method comprising: applying beta radiation from a radioisotope that emits beta radiation to a target area of the eye, and wherein the target area is at least a portion of the bleb; wherein the beta radiation is effective for reducing inflammation caused by the foreign body, and wherein the target area is from 2 to 12 mm in diameter.

\* \* \* \* \*